US012371672B2

(12) United States Patent
Clark et al.

(10) Patent No.: US 12,371,672 B2
(45) Date of Patent: *Jul. 29, 2025

(54) COMPOSITIONS AND METHODS FOR ANTIGEN TARGETING TO CD180

(71) Applicant: UNIVERSITY OF WASHINGTON, Seattle, WA (US)

(72) Inventors: Edward Clark, Seattle, WA (US); Jay Wesley Chaplin, Seattle, WA (US)

(73) Assignee: UNIVERSITY OF WASHINGTON, Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/665,920

(22) Filed: May 16, 2024

(65) Prior Publication Data
US 2024/0301364 A1 Sep. 12, 2024

Related U.S. Application Data

(63) Continuation of application No. 18/063,823, filed on Dec. 9, 2022, now Pat. No. 12,018,291, which is a continuation of application No. 16/731,846, filed on Dec. 31, 2019, now Pat. No. 11,549,102, which is a continuation of application No. 16/245,459, filed on Jan. 11, 2019, now Pat. No. 10,563,179, which is a continuation of application No. 14/426,635, filed as application No. PCT/US2013/059898 on Sep. 16, 2013, now Pat. No. 10,196,614.

(60) Provisional application No. 61/702,368, filed on Sep. 18, 2012.

(51) Int. Cl.
| | |
|---|---|
| *C12N 7/00* | (2006.01) |
| *A61K 39/00* | (2006.01) |
| *A61K 39/12* | (2006.01) |
| *A61K 39/29* | (2006.01) |
| *A61K 39/385* | (2006.01) |
| *A61K 47/68* | (2017.01) |
| *C07K 16/28* | (2006.01) |

(52) U.S. Cl.
CPC .............. *C12N 7/00* (2013.01); *A61K 39/12* (2013.01); *A61K 39/29* (2013.01); *A61K 39/385* (2013.01); *A61K 47/6811* (2017.08); *A61K 47/6849* (2017.08); *C07K 16/2896* (2013.01); *A61K 2039/55511* (2013.01); *A61K 2039/55561* (2013.01); *A61K 2039/6056* (2013.01); *C07K 2319/40* (2013.01); *C07K 2319/74* (2013.01); *C12N 2770/24132* (2013.01); *C12N 2770/24134* (2013.01); *C12N 2770/28033* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 8,058,400 B2 | 11/2011 | Figdor et al. | |
| 9,260,529 B2 * | 2/2016 | Hayden-Ledbetter | ...................... C07K 16/2896 |
| 9,416,188 B2 | 8/2016 | Chaplin et al. | |
| 10,196,612 B1 | 2/2019 | Patel et al. | |
| 10,196,614 B2 * | 2/2019 | Clark | .................... A61K 39/385 |
| 10,563,179 B2 * | 2/2020 | Clark | ................. A61K 47/6849 |
| 11,549,102 B2 * | 1/2023 | Clark | ................. A61K 47/6849 |
| 12,018,291 B2 * | 6/2024 | Clark | ........................ A61P 1/16 |
| 2008/0260751 A1 | 10/2008 | Karp | |
| 2011/0044894 A1 | 2/2011 | Karsunsky | |
| 2012/0020956 A1 | 1/2012 | Chaplin | |
| 2012/0039806 A1 | 2/2012 | Lahoud | |

FOREIGN PATENT DOCUMENTS

WO 2010/042863 A1 4/2010

OTHER PUBLICATIONS

International Search Report for PCT/US2013/059898 mailed Nov. 15, 2013.
Caminschi, et al. "Boosting antibody responses by targeting antigens to dendritic cells," Trends in Immunology, Feb. 2012, 33(2): 71-77.
Caminschi, et al., "Enhancing immune responses by targeting antigen to DC," European Journal of Immunology, Apr. 2009, 39(4): 931-938.
Chaplin, et al., "Anti-CD180 (RP105) activates B cells to rapidly produce polyclonal Ig via a T cell and MyD88—independent pathway," Journal of Immunology, Oct. 2011, 187(8): 4199-4209.
Chaplin, et al., "Targeting antigens to CD180 rapidly induces antigen-specific IgG, affinity maturation, and immunological memory," The Journal of Experimental Medicine Sep. 2013, 210(10): 2135-5146.
Divanovic, et al., "negative regulation of toil-like receptor 4 signaling by the toll-like receptor homolog RP105," Nature Immunology, Jun. 2005, 6(6): 571-578.
Alving, C.R., K.K. Peachman, M. Rao and S.G. Reed 2012. Adjuvants for human vaccines. Curr. Opin. Immunol. 24:310-315.
Aranburu, A., C. Ceccarelli, E. Giorda, R. Lasorella, G. Ballatore, and R. Carsetti. 2010. TLR ligation triggers somatic hypermutation in transitional B cells inducing the generation of IgM memory B cells. J. Immunol. 185:7293-301.
Berkowska, M.A., G.J. Driessen, V. Bikos, C. Grosserichter-Wagener, K. Stamatopoulos, A. Cerutti, B. He, K. Biermann, J.F. Lange, M. van der Burg, J.J. van Dongen, and M.C. van Zelm. Human memory B cells originate from three distinct germinal center-dependent and—independent maturation pathways. Blood. 118:2150-2158.
Borriello, F., M.P. Sethna, S.D. Boyd, A.N. Schweitzer, E.A. Tivol, D. Jacoby, T.B. Strom, E. M. Simpson, G.J. Freeman, and A.H. Sharpe. 1997. B7-1 and B7-2 have overlapping, critical roles in immunoglobulin class switching and germinal center formation. Immunity. 6:303-313.

(Continued)

*Primary Examiner* — Agnieszka Boesen
(74) *Attorney, Agent, or Firm* — McDonnell Boehnen Hulbert & Berghoff

(57) ABSTRACT

The present invention provides compositions of CD180 targeting molecules coupled to heterologous antigens, and their use in treating and/or limiting disease.

20 Claims, 28 Drawing Sheets

(56) References Cited

OTHER PUBLICATIONS

Bowick, G.C., and A.J. McAuley. 2011. Vaccine and adjuvant design for emerging viruses: mutations, deletions, segments and signaling. Bioeng. Bugs. 2:129-35.

Capolunghi, F., S. Cascioli, E. Giorda, M.M. Rosado, A. Plebani, C. Auriti, G. Seganti, R. Zuntini, S. Ferrari, M. Cagliuso, I. Quinti, and R. Carsetti. 2008. CpG drives human transitional B cells to terminal differentiation and production of natural antibodies. J. Immunol. 180:800-8.

Carter, R.W., C. Thompson, D.M. Reid, S.Y. Wong, and D.F. Tough. 2006. Preferential induction of CD4+ T cell responses through in vivo targeting of antigen to dendritic cell-associated C-type lectin-1. J. Immunol. 177:2276-2284.

Chan, V.W., I. Mecklenbrauker, I. Su, G. Texido, M. Leitges, R. Carsetti, C. A. Lowell, K. Rajewsky, K. Miyake, and A. Tarakhovsky. 1998. The molecular mechanism of B cell activation by Toll-like receptor protein RP-105. J. Exp. Med. 188:93-101.

Chappell, C.P., K.E. Draves, N.V. Giltiay, and E.A. Clark. 2012. Extrafollicular B cell activation by marginal zone dendritic cells drives T cell-dependent antibody responses. J. Exp. Med. 209:1825-1840.

Clark, E.A., and G. Shu. 1990. Association between IL-6 and CD40 signaling. IL-6 induces phosphorylation of CD40 receptors. J. Immunol. 145:1400-6.

Clark, E.A., G.L. Shu, B. Lüscher, K.E. Draves, J. Banchereau, J.A. Ledbetter, and M.A. Valentine. 1989. Activation of human B cells. Comparison of the signal transduced by IL-4 to four different competence signals. J. Immunol. 143:3873-80.

Defrance, T., M. Taillardet, and L. Genestier. 2011. T cell-independent B cell memory. Curr. Opin. Immunol. 23:330-6.

Denis, O., D. Latinne, F. Nisol, and H. Bazin. 1993. Resting B cells can act as antigen presenting cells in vivo and induce antibody responses. Int. Immunol. 5:71-8.

Dudziak, D., A.O. Kamphorst, G.F. Heidkamp, V.R. Buchholz, C. Trumpfheller, S. Yamazaki, C. Cheong, K. Liu, H.W. Lee, C.G. Park, R.M. Steinman, and M.C. Nussenzweig. 2007. Differential antigen processing by dendritic cell subsets in vivo. Science. 315:107-11.

Fink, K., K.S. Lang, N. Manjarrez-Orduno, T. Junt, B.M. Senn, M. Holdener, S. Akira, R.M. Zinkernagel, and H. Hengartner. 2006. Early type I interferon-mediated signals on B cells specifically enhance antiviral humoral responses. Europ. J. Immunol. 36:2094-2105.

Finkelman, F.D., J. Ohara, D. K. Goroff, J. Smith, N. Villacreses, J. J. Mond, and W. E. Paul. 1986. Production of BSF-1 during an in vivo, T-dependent immune response. J. Immunol. 137:2878-2885.

Goins, C.L., C.P. Chappell, R. Shashidharamurthy, P. Selvaraj, and J. Jacob. 2010. Immune complex-mediated enhancement of secondary antibody responses. J. Immunol. 184:6293-8.

Han, J.H., S. Akira, K. Calame, B. Beutler, E. Selsing E, and T. Imanishi-Kari. 2007. Class switch recombination and somatic hypermutation in early mouse B cells are mediated by B cell and Toll-like receptors. Immunity. 27:64-75.

He, B., et al., 2010. The transmembrane activator TACI triggers immunoglobulin class switching by activating B cells through the adaptor MyD88. Nat. Immunol. 11:836-845.

Hebeis, B.J., E. Vigorito, and M. Turner. 2004. The p110delta subunit of phosphoinositide 3-kinase is required for the lipopolysaccharide response of mouse B cells. Biochem. Soc. Trans. 32:789-791.

Hebeis, B.J., E. Vigorito, D. Kovesdi, and M. Turner. 2005. Vav proteins are required for B-lymphocyte responses to LPS. Blood. 106:635-640.

Herzenberg, L.A., S. J. Black, T. Tokuhisa, and L. A. Herzenberg. 1980. Memory B cells at successive stages of differentiation. Affinity maturation and the role of IgD receptors. J. Exp. Med. 151:1071-1087.

Kaji, T., A. Ishige, M. Hikida, J. Taka, A, Hijikata, M. Kubo, T. Nagashima, Y. Takahashi, T. Kurosaki, M. Okada, O. Ohara, K. Rajewsky, and T. Takamori. 2012. Distinct cellular pathways select germline-encoded and somatically mutated antibodies into immunological memory. J. Exp. Med. 209:2079-97.

Kawabe, T., T. Naka, K. Yoshida, T. Tanaka, H. Fujiwara, S. Suematsu, N. Yoshida, T. Kishimoto, and H. Kikutani. 1994. The immune responses in CD40-deficient mice: impaired immunoglobulin class switching and germinal center formation. Immunity. 1:167-178.

Kawamura, H., and J.A. Berzofsky. 1986. Enhancement of antigenic potency in vitro and immunogenicity in vivo by coupling the antigen to anti-immunoglobulin. J. Immunol. 136:58-65.

Kovesdi, D., K. Paszty, A. Enyedi, E. Kiss, J. Matko, K. Ludanyi, E. Rajnavolgyi, and G. Sarmay. 2004. Antigen receptor-mediated signaling pathways in transitional immature B cells. Cell Signal. 16:881-9.

Kuraoka, M., D. Liao, K. Yang, S.D. Allgood, M.C. Levesque, G. Kelsoe, and Y. Ueda. 2009. Activation-induced cytidine deaminase expression and activity in the absence of germinal centers: insights into hyper-IgM syndrome. J. Immunol. 183:3237-48.

Kuraoka, M., L. McWilliams, and G. Kelsoe. 2011. AID expression during B-cell development: searching for answers. Immunol. Res. 49:3-13.

Caminschi. 2011. Targeting antigen to mouse dendritic cells via Clec9A induces potent CD4 T cell responses biased toward a follicular helper phenotype. J. Immunol. 187:842-50.

Le Bon, A., C. Thompson, E. Kamphuis, V. Durand, C. Rossmann, U. Kalinke, and D.F. Tough. 2006. Cutting edge: enhancement of antibody responses through direct stimulation of B and T cells by type I IFN. J. Immunol. 176:2074-2078.

Levine MM. 2011. "Ideal" vaccines for resource poor settings. Vaccine. 29 Suppl 4:D116-25. Mao, C., L. Jiang, M. Melo-Jorge, M. Puthenveetil, X. Zhang, M.C. Carrol, and T. Imanishi-Kari. 2004. T cell-independent somatic hypermutation in murine B cells with an immature phenotype. Immunity. 20:133-44.

Markowitz, J.S., P.R. Rogers, M.J. Grusby, D.C. Parker, and L.H. Glimcher. 1993. B lymphocyte development and activation independent of MHC class II expression. J. Immunol. 150:1223-33.

Miller, M.A., and M.H. Rathore. 2012. Immunization in special populations. Adv. Pediatr. 59:95-136.

Miyake, K., Y. Yamashita, Y. Hitoshi, K. Takatsu, and M. Kimoto. 1994. Murine B cell proliferation and protection from apoptosis with an antibody against a 105-kD molecule: unresponsiveness of X-linked immunodeficient B cells. J. Exp. Med. 180:1217-1224.

Miyake, K., Y. Yamashita, M. Ogata, T. Sudo, and M. Kimoto. 1995. RP105, a novel B cell surface molecule implicated in B cell activation, is a member of the leucine-rich repeat protein family. J. Immunol. 154:3333-3340.

Nagai, Y., T. Kobayashi, Y. Motoi, Y. Ishiguro, S. Akashi, S. Saitoh, Y. Kusumoto, T. Kaisho, S. Akira, M. Matsumoto, K. Takatsu, and K. Miyake. 2005. The radioprotective 105/MD-1 complex links TLR2 and TLR4/MD-2 in antibody response to microbial membranes. J Immunol. 174:7043-9.

Rappuoli, R., C.W. Mandl, S. Black, and E. De Gregorio. 2011. Vaccines for the twenty-first century society. Nat. Rev. Immunol. 11:865-72.

Rickert, R.C., J. Jellusova, and A.V. Miletic. 2011. Signaling by the tumor necrosis factor receptor superfamily in B-cell biology and disease. Immunol. Rev. 244:115-33.

Sancho, D., and C. Reis e Sousa. 2012. Signaling by myeloid C-type lectin receptors in immunity and homeostasis. Annu. Rev. Immunol. 30:491-529.

Sasaki, Y., S. Casola, J. L. Kutok, K. Rajewsky, and M. Shmidt-Supprian. 2004. TNF family member B cell-activating factor (BAFF) receptor-dependent and —independent roles for BAFF in B cell physiology. J. Immunol. 173:2245-2252.

Shih, T. A., M. Roederer, and M. C. Nussenzweig. 2002. Role of antigen receptor affinity in T cell-independent antibody responses in vivo. Nat. Immunol. 3:399-406.

Snider, D.P.. and D.M. Segal. 1989. Efficiency of antigen presentation after antigen targeting to surface IgD, IgM, MHC II, Fc gamma RII, and B220 molecules on murine splenic B cells. J. Immunol. 143:59-65.

(56) References Cited

OTHER PUBLICATIONS

Taylor, J.J., M.K. Jenkins, and KA. Pape. 2012. Heterogeneity in the differentiation and function of memory B cells. Trends Immunol. 33:590-7.

Ueda, Y., D. Liao, K. Yang, A. Patel, and G. Kelsoe. 2007. T-independent activation-induced cytidine deaminase expression, class-switch recombination, and antibody production by immature/transitional 1 B cells. J. Immunol. 178:3593-601.

Valentine, M.A., E. A. Clark, G. L. Shu, N.A. Norris, and J.A. Ledbetter. 1988. Antibody to a novel 95-kDa surface glycoprotein on human B cells induces calcium mobilization and B cell activation. J. Immunol. 140:4071-4078.

Weir, D.M., L. A. Herzenberg, C. Blackwell, and L. A. Herzenberg. 1986. Handbook of Experimental Immunology. 1:31.6-31.7.

Weller, S., A. Faili, C. Garcia, M.C. Braun, F.F. Le Deist, G.G. de Sainte Basile, O. Hermine, A. Fischer, C.A. Reynaud, and J.C. Weill. 2001. CD40-CD40L independent lg gene hypermutation suggests a second B cell diversification pathway in humans. Proc. Natl. Acad. Sci. U S A. 98:1166-70.

Yazawa, N., M. Fujimoto, S. Sato, K. Miyake, N. Asano, Y. Nagai, O. Takeuchi, K. Takeda, H. Okochi, S. Akira, T.F. Tedder, and K. Tamaki. 2003. CD19 regulates innate immunity by the Toll-like receptor RP105 signaling in B lymphocytes. Blood 102:1374-1380.

Zhang, J., Y.J. Liu, I.C. MacLennan, D. Gray, and P.L. Lane. 1988. B cell memory to thymus-independent antigens type 1 and type 2: the role of lipopolysaccharide in B memory induction. Europ. J. Immunol. 18:1417-24.

Zuckerman and Zuckerman, "Mutations of the surface protein of hepatitis B virus," Antiviral Res 60:75-78, 2003.

Peterson, et al., "Structure of hepatitis B surface antigen. Correlation of subtype with amino acid sequence and location of the carbohydrate moiety," J. Biol. Chem 257:10414-10420, 1982.

Charnay et al. "Localization on the viral genome and nucleotide sequence of the gene coding for the two major polypeptides of the hepatitis B surface antigen (HBs Ag)," Nucleic Acids Res 7:335-346, 1979.

Grakoui, et al. "Expression and identification of hepatitis C virus polyprotein cleavage products," J. Virol 67:1385, 1993.

Choo, et al. "Genetic organization and diversity of the hepatitis C virus," PNAS 88:2451-2458, 1991.

Huse et al., "Generation of a large combinatorial library of the immunoglobulin repertoire in phage lambda," Science 246:1275-1281 (1989).

Ward et al., "Binding activities of a repertoire of single immunoglobulin variable domains secreted from *Escherichia coli*," Nature 341:544-546 (1989).

Vaughan et al., "Human antibodies with sub-nanomolar affinities isolated from a large non-immunized phage display library," Nature Biotech. 14:309-314 (1996).

Mao, et al., "T cell-Independent Somatic Hypermutation in Murine B cells with an Immature Phenotype," Feb. 2004, Immunity, 20:133-144.

Miura et al. RP105 is associated with MD-1 and transmits an activation signal in human B cells Blood (1998) vol. 92 (8), pp. 2815-2822.

* cited by examiner

COMPOSITIONS AND METHODS FOR ANTIGEN TARGETING TO CD180

STATEMENT OF GOVERNMENT RIGHTS

This invention was made with government support under Grant Nos. AI052203 and AI044257, awarded by the National Institutes of Health. The government has certain rights in the invention

BACKGROUND

Current vaccination strategies require T cell help to produce IgG class antibodies, consequently they fail in patients with T cell deficiencies (DiGeorge Syndrome, AIDS) or defects in co-stimulation between B and T cells (Hyper-IgM Syndrome from lack of CD40-CD40 ligand interaction). Antigen targeting is a method where an immunization material (antigen) is coupled to a monoclonal antibody that when injected both delivers the antigen and leads to a stimulatory signal to the antibody producing B cell. Published antigen targeting strategies directed at CD40 or DEC-205 on dendritic cells enhance IgG production but still require functional T cells for this effect. Thus, improved compositions and methods are needed.

SUMMARY OF THE INVENTION

In a first aspect, the present invention provides compositions, comprising:
(a) a CD180 targeting molecule; and
(b) a heterologous antigen attached to the CD 180 targeting molecule.

In various embodiments, the heterologous antigen is a polypeptide, carbohydrate, polysaccharide, or glycolipid antigen. In various further embodiments, the antigen is an allergen.
or a pathogen-specific antigen. In specific embodiments, the pathogen-specific antigen comprises an antigen selected from the group consisting of a West Nile virus antigen, a hepatitis virus antigen, and a dengue virus antigen. In another embodiment, the CD180 targeting molecule is a CD180 antibody or antibody fragment. In a further embodiment, the CD180 targeting molecule is a CD180 antibody or antibody fragment, and wherein the heterologous antigen is a polypeptide. In another embodiment, the composition further comprises an adjuvant, such as toll-like receptor 7 (TLR7) agonists and TLR9 agonist.

In another aspect, the invention provides isolated nucleic acids encoding the compositions of the invention where the antigen is a polypeptide. In a further aspect, the invention provides nucleic acid vector comprising the isolated nucleic acids of the invention. In another aspect, the invention provides recombinant host cells comprising the nucleic acid vectors of the invention. In a still further aspect, the invention provides pharmaceutical compositions, comprising a composition according to any embodiment or combination of embodiments of the invention, and a pharmaceutically acceptable carrier.

In a further aspect, the invention provided methods for producing antibody, comprising culturing the recombinant host cells of the invention under conditions suitable for expression of the nucleic-acid encoded antibody composition; and isolating the antibody composition from the cultured cells.

In a still; further aspect, the invention provides methods for treating or limiting development of a disorder, comprising administering to an individual at risk of a disorder or having a disorder, an amount effective to treat or limit development of the disorder of a composition according to any embodiment or combination of embodiments of the invention, or pharmaceutically acceptable salts thereof. In one embodiment, the individual has a T-cell deficiency and/or a defect in co-stimulation between B cells and T cells. In another embodiment, the individual is a neonate or is elderly. In further embodiments, the individual has an allergy, a congenital or acquired immunodeficiency, has been exposed to an infectious agent, has one or more conditions selected from the group consisting of ataxia-telangiectasia, hyper-IgM syndrome, DiGeorge Syndrome, Wiscott-Aldrich Syndrome, Common Variable Immunodeficiency Syndromes, Polysaccharide response defects including Selective Antibody Deficiency with Normal Immunoglobulins (SADNI), viral infection, cancer, hepatitis, diabetes, and immunosuppression following bone marrow or organ transplants or cytotoxic/myeloablative therapy; or is a pregnant female, asplenic, taking drugs that cause myelosuppression or reduction in lymphocytes, receiving radiation therapy, and/or has chronic renal failure.

Figure 4A:
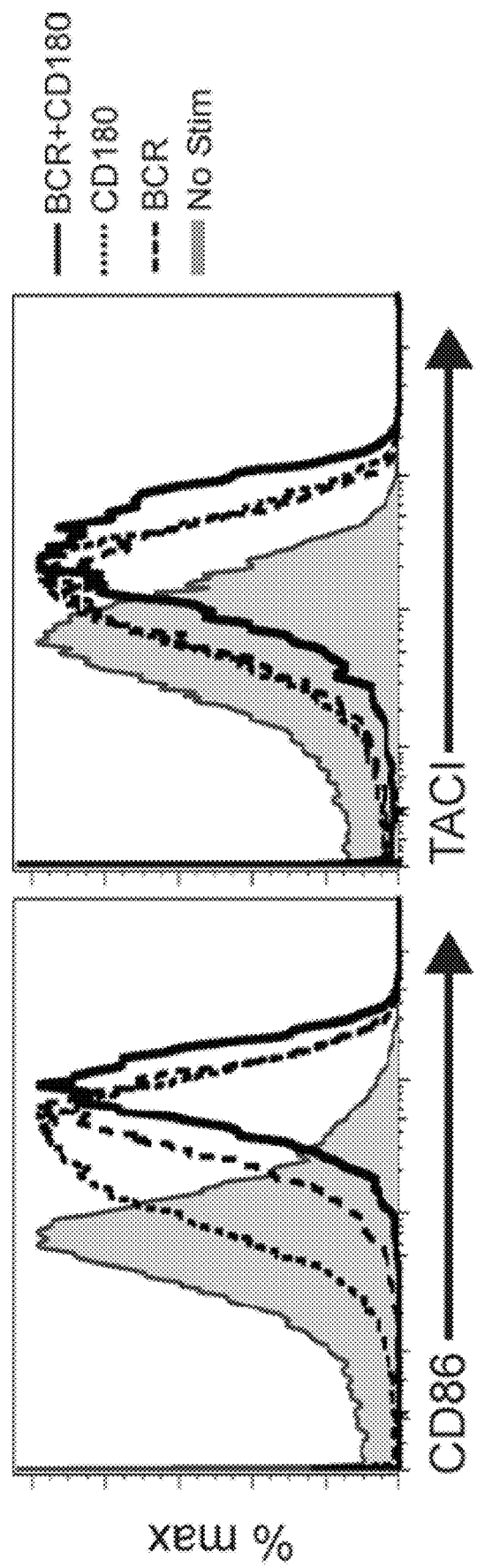
Figure 4B:
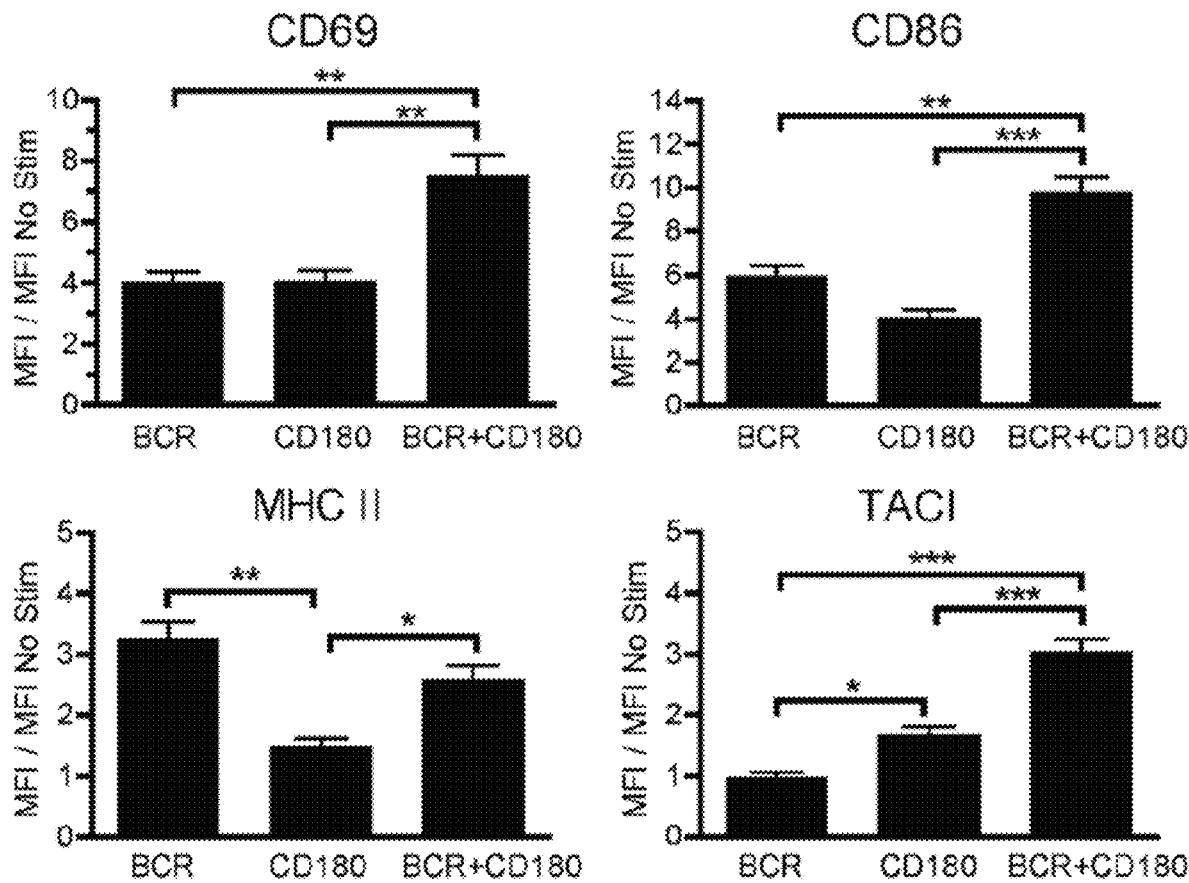

FIG. 4A-4B. Ag-specific B cells are efficiently activated in vivo by combined signaling through BCR and CD180. (A, B) Groups of B1-8hi mice (9 mice/group) were inoculated with either 100 μg NP-isotype or NP-αCD180 and spleens were harvested 24 h later (A and B) or 48 and 72 h later (data not shown). The NP-specific B cells (6-10%) were distinguished from total CD19+ B cells by staining with NP-APC. Four groups of CD19+ B cells were then analyzed ex vivo for their expression of CD69, CD86, MHC class II, and TACI: unstimulated B cells (NP− B cells from NP-isotype-treated mice, gray in (A); B-cell receptor (BCR)-stimulated B cells (NP+ B cells from NP-isotype treated mice); CD180-stimulated B cells (NP− B cells from NP-αCD180 treated mice); and B cells stimulated through both the BCR and CD180 stimulated (NP+ B cells from NP-αCD180 treated mice). (A) Histograms show CD86 and TACI expression on B220+ B cells stimulated as indicated 24 h post-immunization. (B) Mean fluorescent intensities at 24 h post-immunization are plotted for the indicated surface markers relative to unstimulated control B cells (value 1.0). Similar data were obtained at 48 and 72 h post-immunization. A representative experiment of three experiments is shown.

Figure 5A:
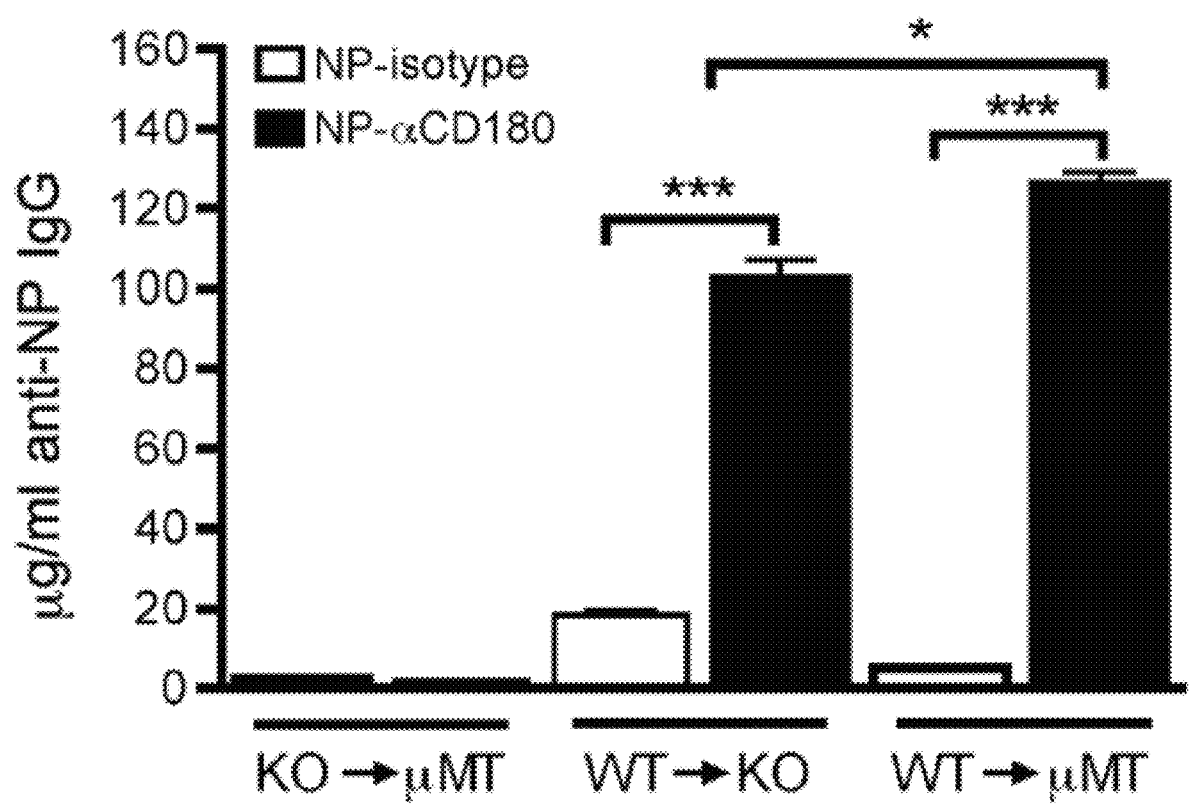
Figure 5B:
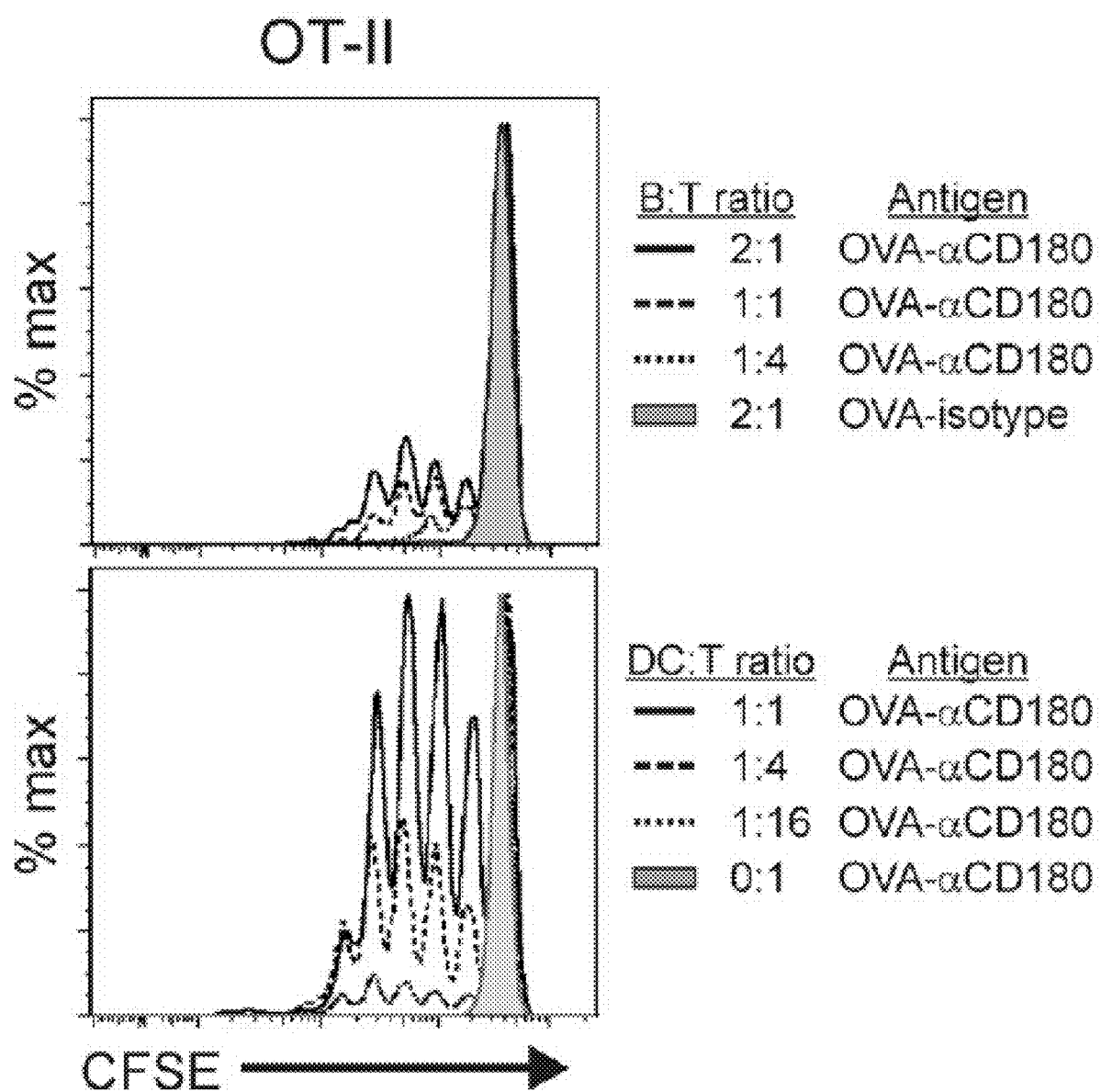
Figure 5C:
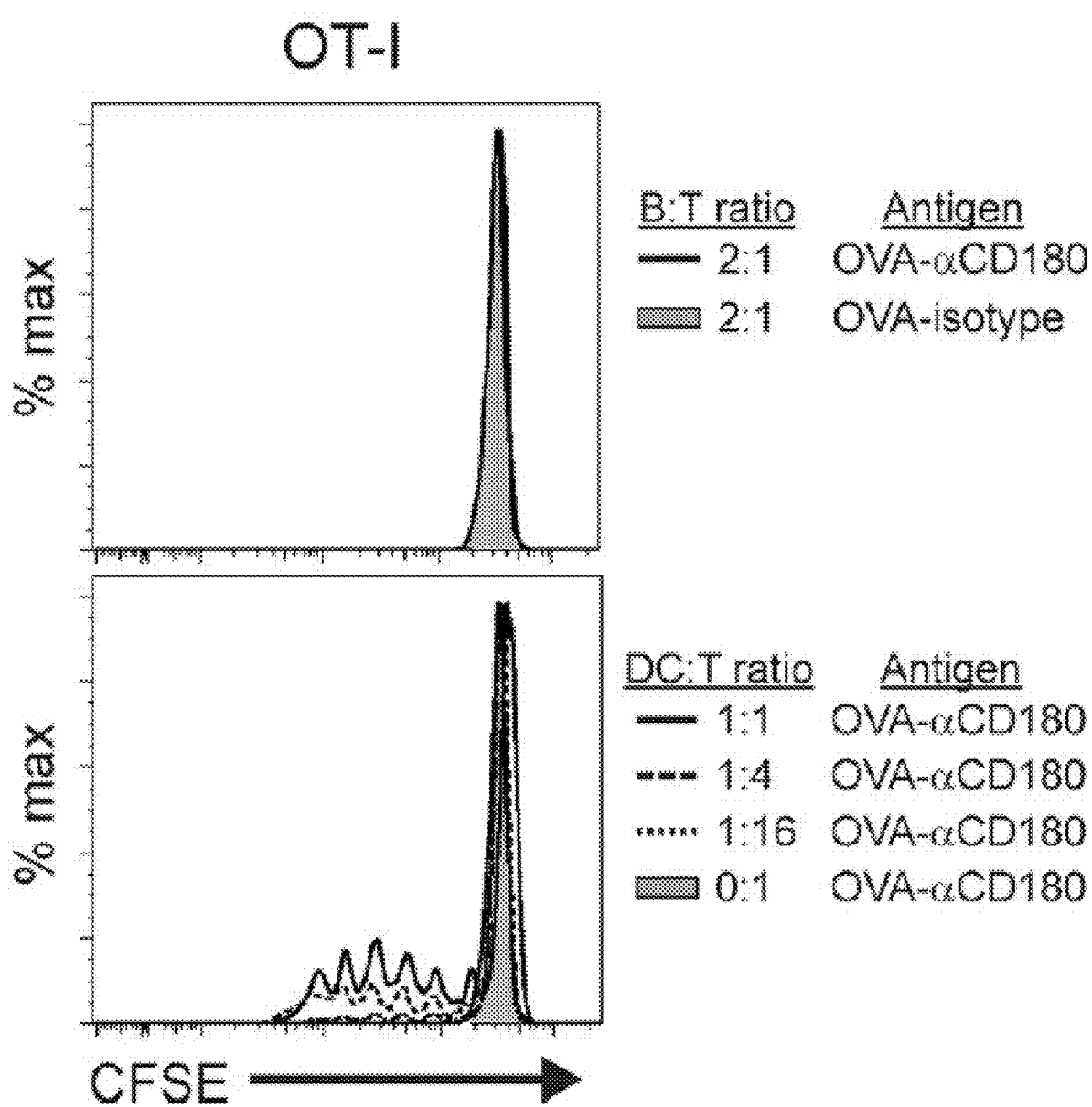

FIG. 5A-5C. CD180 Ag-targeting responses require expression on B cells and not on non-B cells. (A) Schematic of adoptive transfers. 10×10⁶ B cells purified from either WT or CD180 KO mice were transferred to μMT or CD180 KO recipients as indicated. 24 h following transfer, mice were inoculated with 100 μg of NP-isotype or NP-αCD180 and bled 10 d later. (B) NP-specific IgG responses at d 10 of groups shown in (A) after inoculation with 100 μg NP-αCD180 (black) or NP-isotype (white) analysis by ELISA. Three mice/group; representative of two experiments. * $p<0.05$; *** $p<0.001$. (C) WT mice were inoculated with 100 μg OVA-αCD180 or OVA-isotype and spleens harvested 16 h later. B cells and DCs were purified by negative selection, then seeded at indicated ratios into culture with CFSE-labeled purified OT-II T cells at the indicated ratios; CFSE dilution of CD4+Vα2 TCR+ cells was assessed following 72 h in culture. Co-cultures performed in triplicate, representative of two independent experiments for C.

Figure 6A:
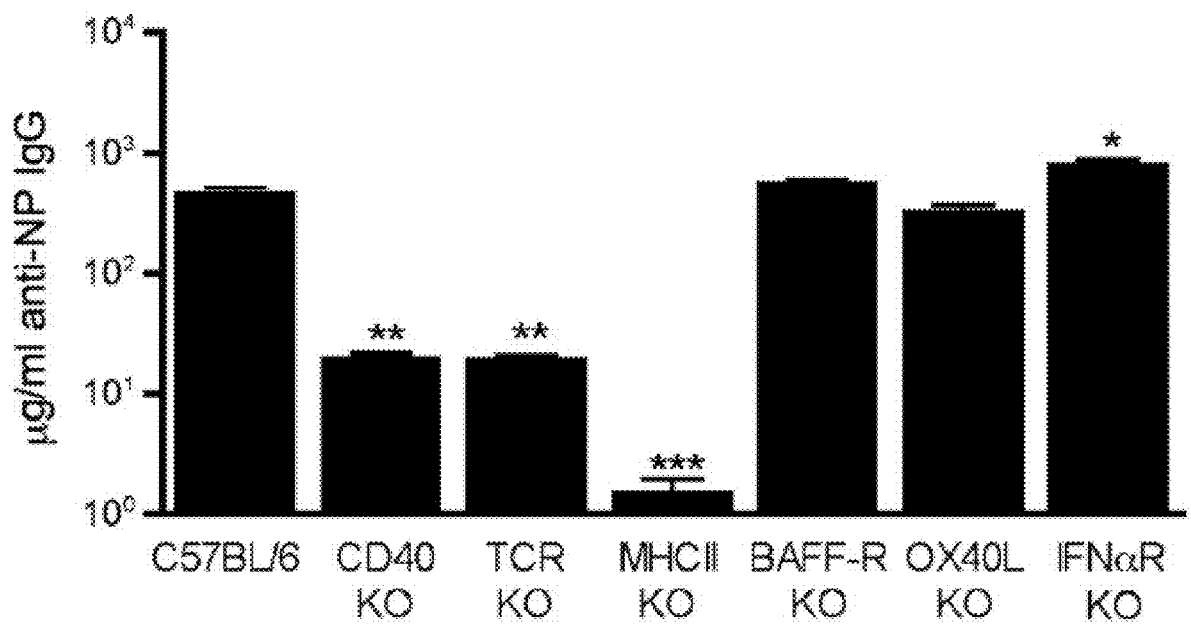
Figure 6B:
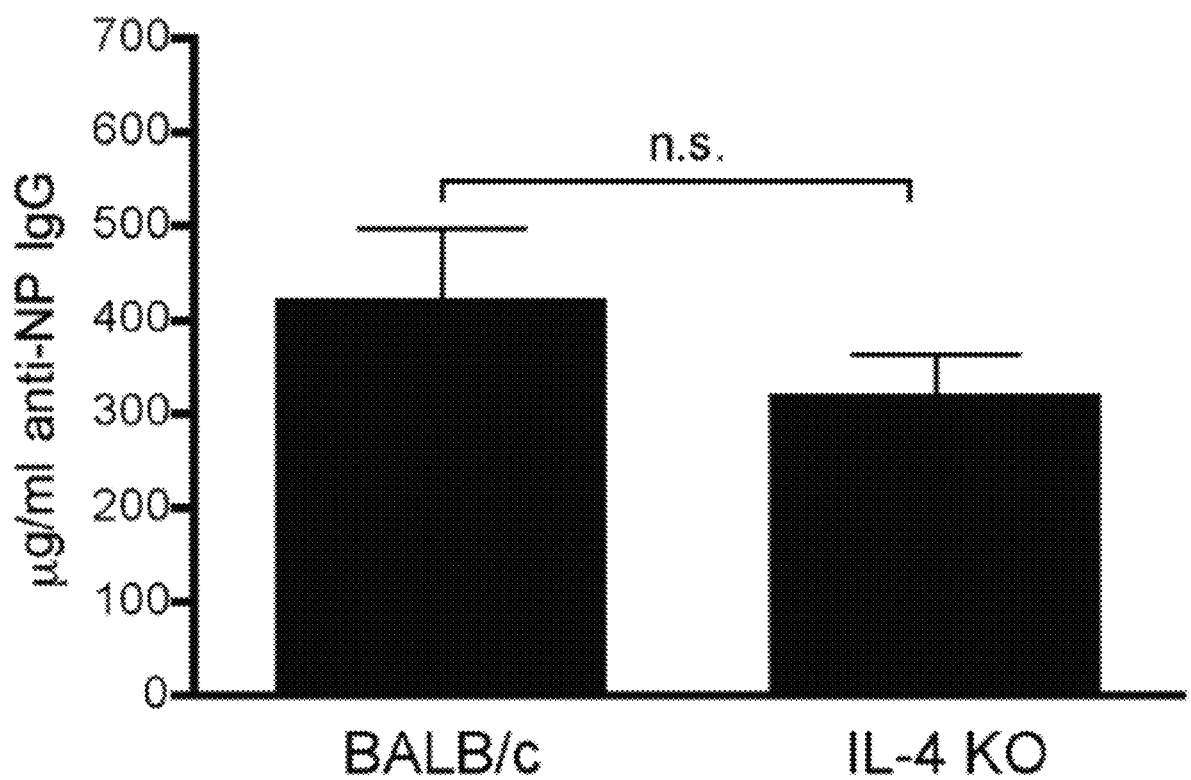
Figure 6C:
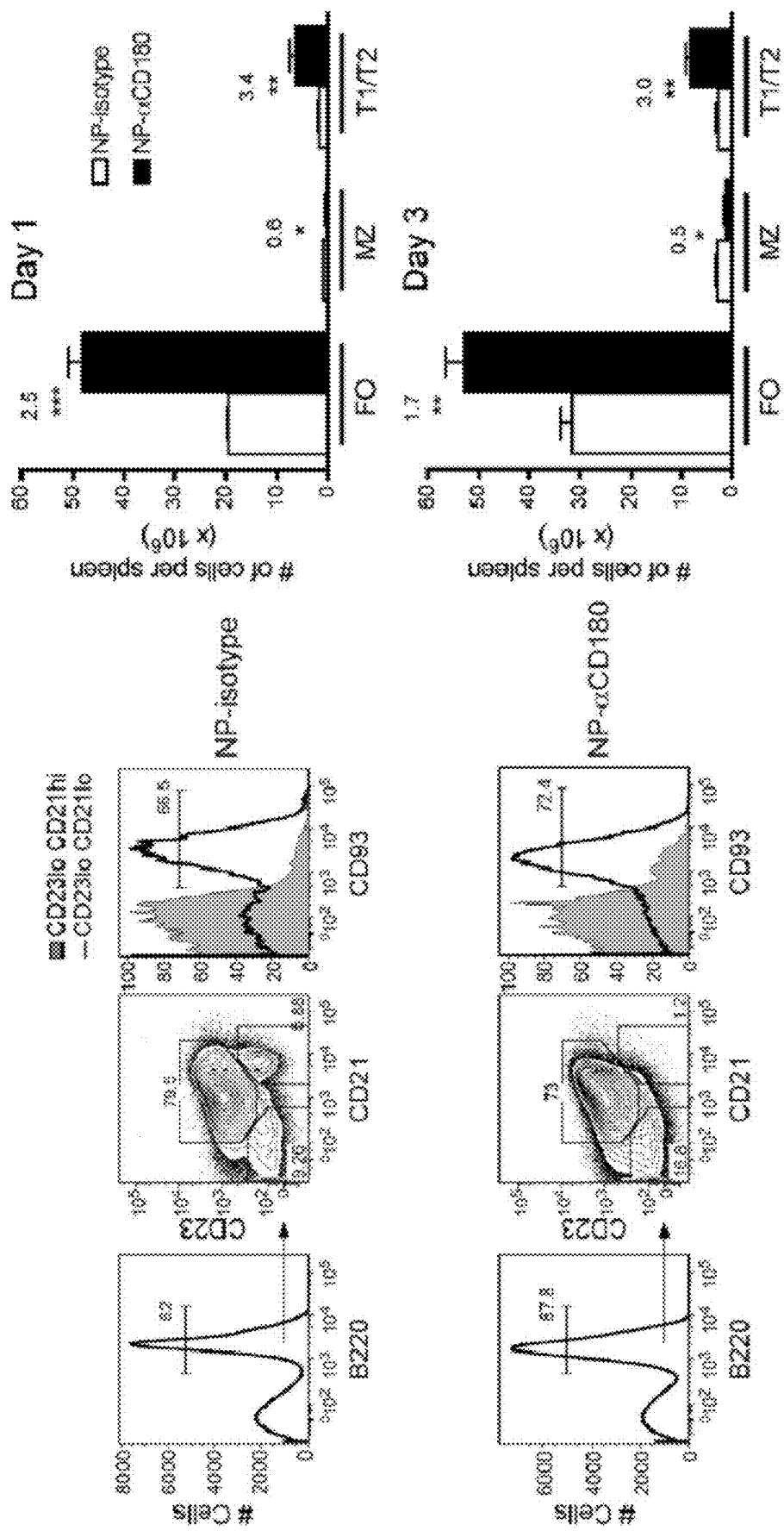

FIG. 6A-6C. MHC class II is required for Ag targeting to CD180 but not BAFF-R, IFNα/β, IL-4 or OX40L. (A, B) WT C57BL/6 mice and the indicated KO mice (A) or BALB/c mice (B) were inoculated with 100 μg NP-αCD180 or NP-isotype, and bled at d 10; levels of NP-specific IgG Abs were determined by ELISA. Three mice/group; representative of two experiments for both A and B. * $p<0.05$;  $p<0.01$; * $p<0.001$ as determined by one-way ANOVA with Bonferonni post-tests by comparing to WT controls. (C) Groups of WT mice were immunized with 100 μg NP-αCD180 or NP-isotype and sacrificed on days 1 and 3 p.i. for analysis of splenic B cell subsets. Flow cytometry plots show gating strategy used to enumerate FO (B220+CD23hiCD21int), MZ (B220+CD23loCD21hiCD93−) and T1/T2 transitional (B220+CD23loCD21loCD93+) B cells (day 1 group shown). Bar graphs depict total number of cells in the spleen (mean+/−SEM) of each subset. Number on graphs indicate fold increase in cell subsets from NP-αCD180-immunized mice compared to isotype controls. Data are from one experiment using 3-4 mice/group/time point. * $p<0.05$;  $p<0.01$; * $p<0.001$ as determined by one-way ANOVA with Bonferonni post-tests.

Figure 7A:
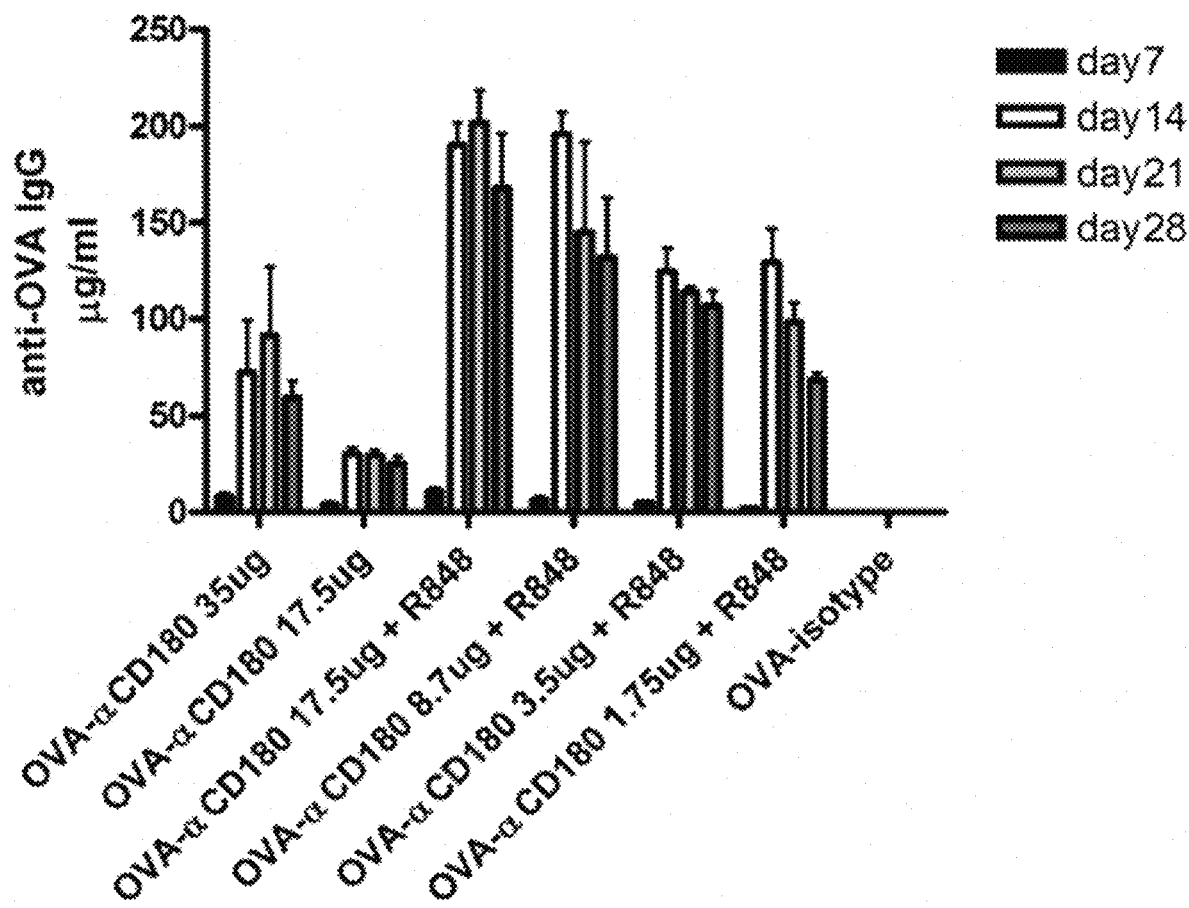
Figure 7B:
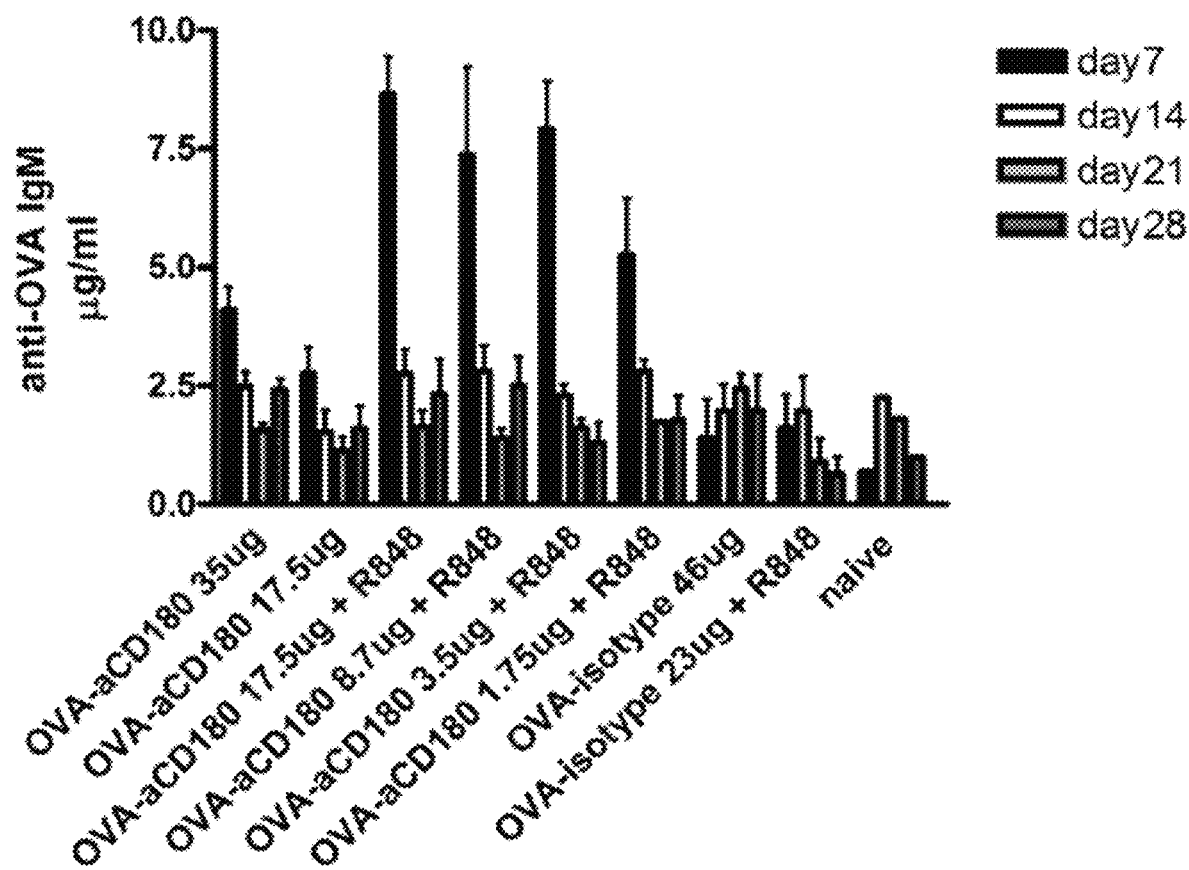

FIG. 7A-7B. Graph showing that combination of an OVA-αCD180 conjugate and a TLR7 agonist provide synergistic induction of (A) IgG and (B) IgM antibody responses.

Figure 8A:
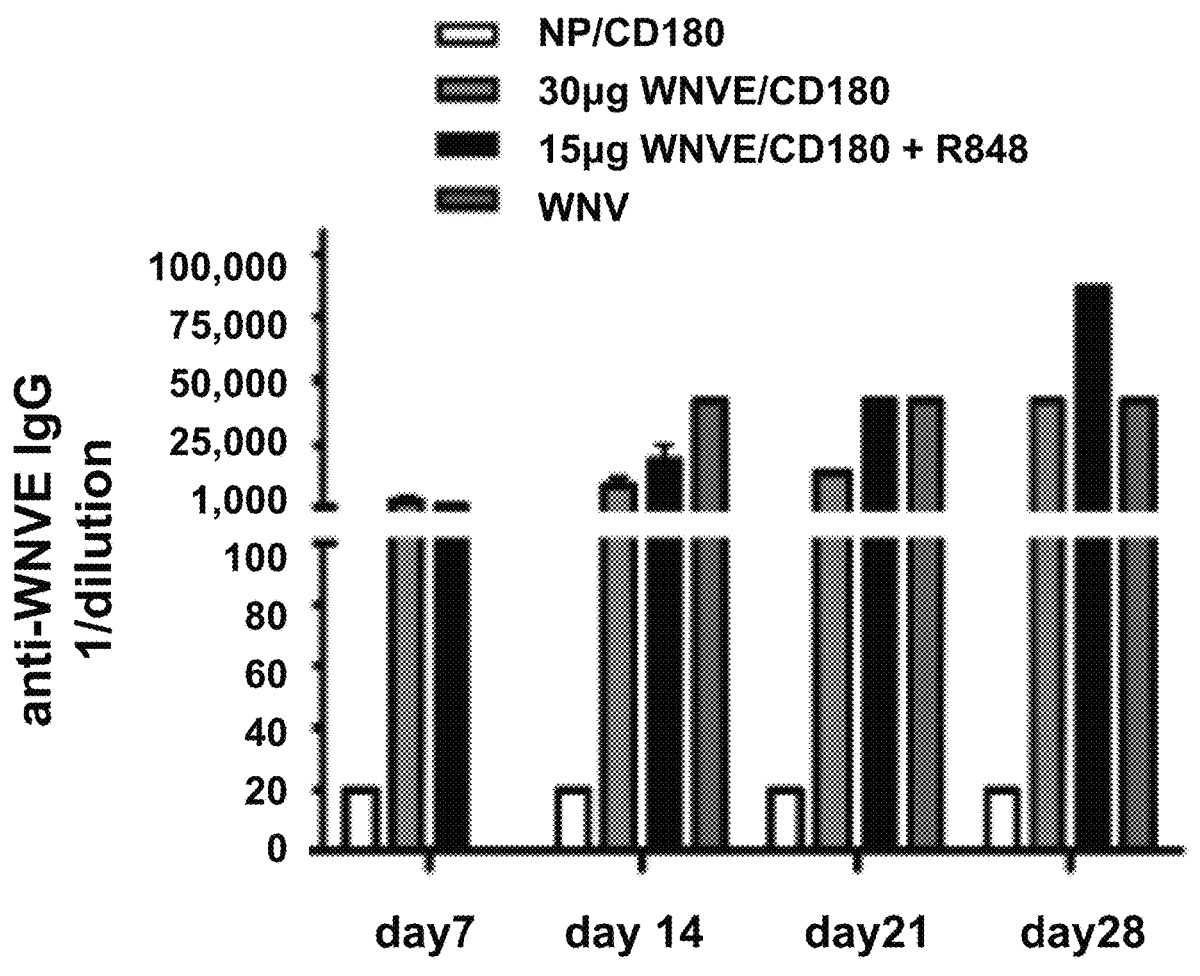
Figure 8B:
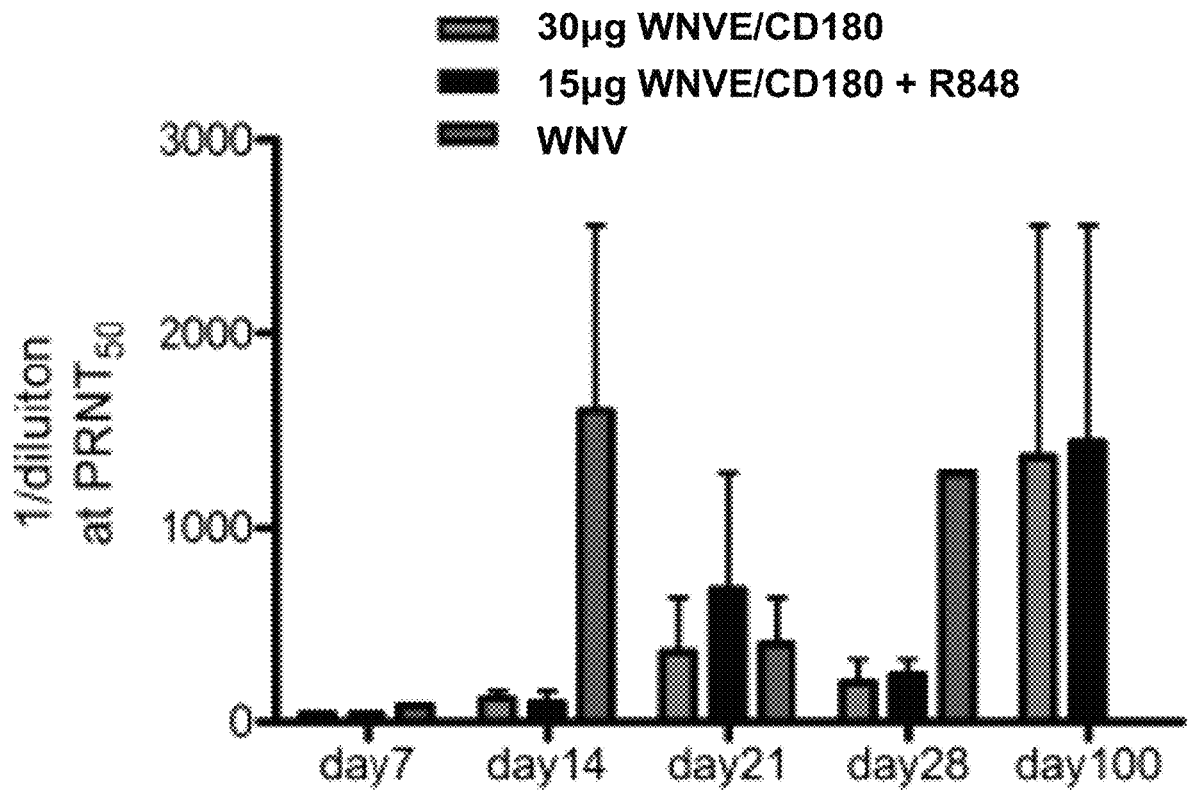

FIG. 8A-8B. Graph showing that mice inoculated with anti-CD180 to which purified recombinant West Nile virus (WNV) envelope (E) protein has been attached (WNVE) develop both (A) WNVE specific IgG Abs and (B) neutralizing Abs to WNVE.

Figure 9:
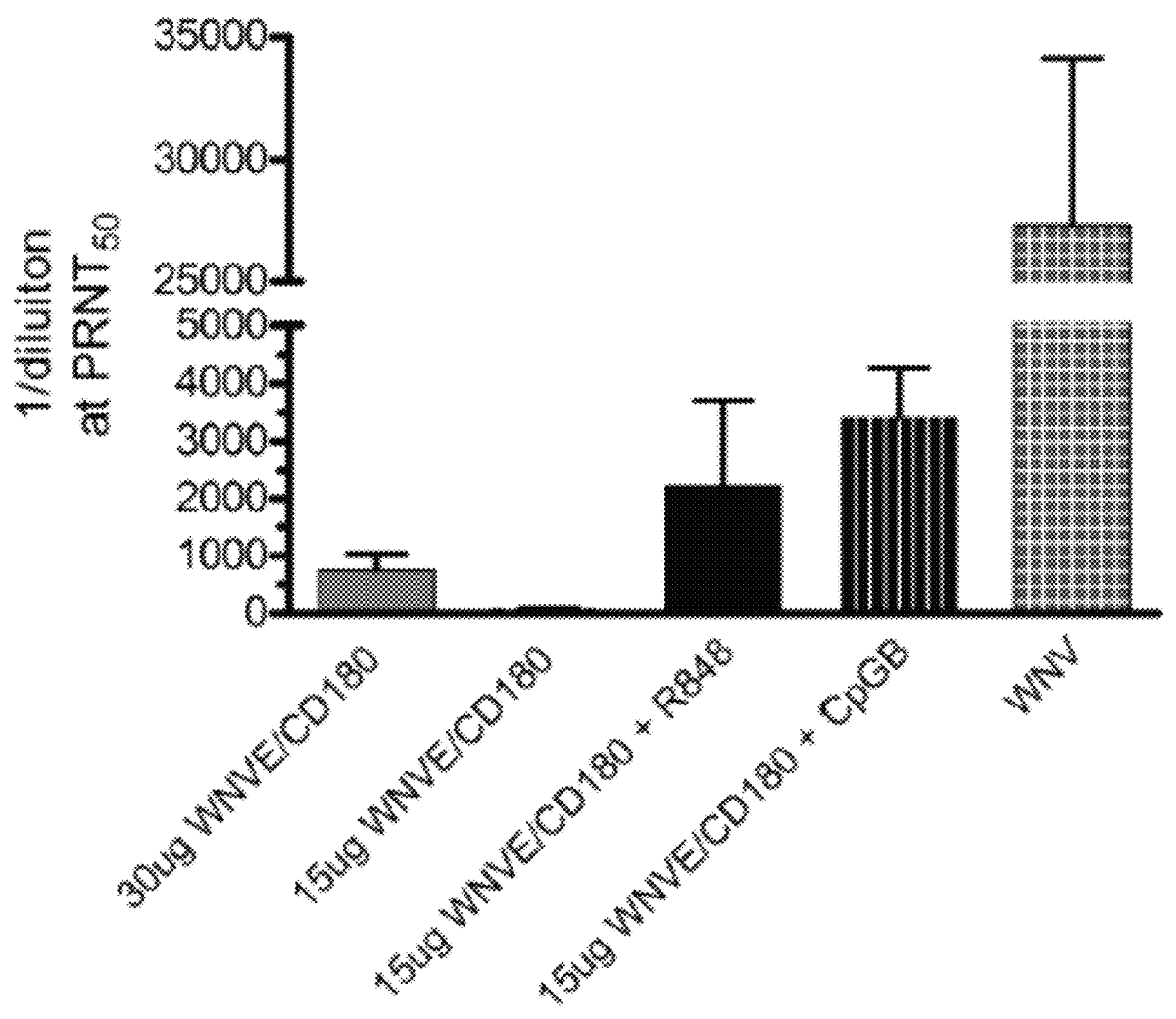

FIG. 9. Graph showing that the WNVE-αCD180 conjugate induces a neutralizing antibody response that is enhanced by the addition of an adjuvant to TLR7 (R848) or TLR9 (CpGB).

DETAILED DESCRIPTION OF THE INVENTION

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, CA), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, CA), *Culture of Animal Cells: A Manual of Basic Technique*, 2$^{nd}$ Ed. (R. I. Freshney. 1987. Liss, Inc. New York, NY), *Gene Transfer and Expression Protocols*, pp. 109-128, ed. E. J. Murray, The Humana Press Inc., Clifton, N.J.), and the Ambion 1998 Catalog (Ambion, Austin, TX).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides compositions, comprising:
(a) a CD180 targeting molecule; and
(b) a heterologous antigen attached to the CD 180 targeting molecule.

The compositions of the invention can be used, for example, in methods targeting antigen to CD180, a surface protein expressed on B cells, macrophages, and dendritic cells, that to produce antigen-specific IgG in the absence of T cell costimulation (such as CD40 deficiency) or the complete absence of T cells (such as TCR B/8 deficiency).

As disclosed herein, the inventors have surprisingly discovered that the compositions of the invention induce rapid activation of antigen (Ag)-specific B cells, leading to significant antigen-specific IgG and IgM production within 7 days. Remarkably, a single injection of Ag-CD180 antibody (αCD180) without any additional adjuvant also led to the development of both antibody (Ab) affinity maturation and immunologic memory.

The CD180 targeting molecule may be any molecule that binds directly to CD180 present in the surface of B cells, macrophages, or dendritic cells. In various non-limiting embodiments, the CD180 targeting molecule may be a polypeptide (such as a peptide mimetic, antibody, etc.), nucleic acid (such as an aptamer), carbohydrate, organic molecule, etc. In a particular embodiment, the CD180 targeting molecule comprises a polypeptide; in one non-limiting embodiment, the polypeptide is an antibody or antibody fragment. As used herein, "antibody" includes reference to an immunoglobulin molecule immunologically reactive with human CD180 (preferably selective for CD180), and includes monoclonal antibodies. Various isotypes of antibodies exist, for example IgG1, IgG2, IgG3, IgG4, and other Ig, e.g., IgM, IgA, IgE isotypes. The term also includes genetically engineered forms such as chimeric antibodies (e.g., humanized murine antibodies) and heteroconjugate antibodies (e.g., bispecific antibodies), fully humanized antibodies, and human antibodies. As used throughout the application, the term "antibody" includes fragments with antigen-binding capability (e.g., Fab', F(ab')2, Fab, Fv and rIgG. See also, Pierce Catalog and Handbook, 1994-1995 (Pierce Chemical Co., Rockford, IL). See also, e.g., Kuby, J., *Immunology*, 3$^{rd}$ Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol*: 5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301. Various antigen binding domain-fusion proteins are also disclosed, e.g., in US patent application Nos. 2003/0118592 and 2003/0133939, and are encompassed within the term "antibody" as used in this application.

An antibody immunologically reactive with human CD180 can be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

In one embodiment, the antibody comprises or consists mAb G28-8, which is commercially available from a number of sources, (Thermo Scientific, Sigma Aldrich, etc.) or a F(ab')2 fragment of mAb G28-8. In a particular embodiment, the antibody comprises a human or animal CD180 binding domain linked to an immunoglobulin constant region (Fc) domain that has impaired binding to human or animal Fc receptor FcγRIIb and/or to human or animal complement proteins. For example, the antibody or fragment thereof may be one such as is described in US patent application publication number 20120020965, incorporated by reference herein in its entirety. For example, the antibody may comprise or consist of a scFv-Fc molecule constructed from the cloned variable regions of mAb G28-8. The Fc domain of the recombinant molecules is an altered human IgG1 Fc domain with three amino acid changes (P238S, P331S, K322S) that reduce the binding of the molecule to Fc-receptors and C1q.

The compositions comprise a "heterologous" antigen, in that the antigen is not naturally present in the CD180 targeting molecule; thus, the compositions comprise a conjugate of the CD180 targeting molecule and the heterologous antigen. The CD180 targeting molecule and the heterologous antigen can be conjugated in any suitable manner, including covalently and non-covalently; any manner that irreversibly links the heterologous Ag to the anti-CD180 should work. The specific manner of conjugation most appropriate for a specific composition will depend on the components utilized, and can be determined by those of skill in the art. In some embodiments, the targeting molecule and the antigen can be conjugated via one or more linker moieties. In embodiments where both the targeting molecule and the antigen are polypeptides, the compositions can be recombinantly expressed as a chimera. For non-recombinantly expressed embodiments, any suitable conjugation technique can be used, including but not limited to engineered disulfide linkages, formalin/glutaraldehyde cross-linking, selective linking (such as is disclosed in the examples that follow), streptavidin/biotin based conjugation, bispecifics with CD180 and tag (FLAG, His, etc.) binding ability could be generated and mixed with tagged Ag or have direct affinity for the Ag, etc.

Since the compositions can be used in methods targeting antigen to CD180 to produce antigen-specific IgG in the absence of T cell costimulation or the complete absence of T cells, it will be clear to those of skill in the art that any suitable antigen can be used in the compositions. The heterologous antigen may be of any compound type, including but not limited to polypeptide, nucleic acid, lipid, polysaccharide, glycolipid, etc. In one embodiment the heterologous antigen comprise a polypeptide. In other embodiments, the heterologous antigen comprises a polysaccharide or a glycolipid antigen.

In one embodiment, the heterologous antigen comprises or consists of a pathogen-specific antigen; the antigen may be from any pathogen of interest in a given situation. In non-limiting embodiments, the pathogen-specific antigens include antigens from hepatitis (A, B, C, E, etc.) virus, human papillomavirus, herpes simplex viruses, cytomegalovirus, Epstein-Barr virus, influenza virus, parainfluenza virus, enterovirus, measles virus, mumps virus, polio virus, rabies virus, human immunodeficiency virus, respiratory syncytial virus, Rotavirus, rubella virus, varicella zoster virus, Ebola virus, cytomegalovirus, Marburg virus, norovirus, variola virus, any Flavivus including but not limited to West Nile virus, yellow fever virus, dengue virus, tick-borne encephalitis virus, and Japanese encephalitis virus; human immunodeficiency virus (HIV), *Bacillus anthracis, Bordetalla pertusis, Chlamydia trachomatis, Clostridium tetani, Clastridium difficile, Corynebacterium diptheriae, Coxiella burnetii, Escherichia coli, Haemophilus influenza, Helicobacter pylori, Leishmania donovani, L. tropica* and *L. braziliensis, Mycobacterium tuberculosis, Mycobacterium leprae, Neisseria meningitis, Plasmodium falciparum, P. ovale, P. malariae* and *P. vivax, Pseudomonas aeruginosa, Salmonella typhi, Schistosoma hematobium, S. mansoni, Streptococcus pneumoniae* (group A and B), *Staphylococcus aureus, Toxoplasma gondii, Trypanosoma brucei, T. cruzi* and *Vibrio cholerae*.

In one non-limiting example, the heterologus antigen is an antigen from West Nile virus (WNV), including but not limited to WNV envelope protein E with an amino acid sequence similar to or identical to those described (T. J Chambers et al., J General Virology 79:2375-2380, 1998) or antigenic fragments thereof. or a WNV nonstructural (NS) protein such as NS2a, NS2b, NS3, NS4a, NS4b or NS5. As shown in the examples that follow, mice inoculated with a CD180 targeting molecule to which purified recombinant West Nile virus (WNV) envelope (E) protein has been attached (WNVE) develop both WNVE specific IgG Abs and neutralizing Abs to WNVE, and that mice immunized with WNVE-CD180 conjugates are protected from death induced by intracranial challenge with WNV. These data are merely exemplary of how the compositions of the invention can be used to induce rapid activation of antigen (Ag)-specific B cells and T cells against any antigen conjugated to the CD180 targeting molecule, leading to significant IgG and IgM production, Ab affinity maturation, and immunologic memory.

In another embodiment, the heterologous antigen is an antigen from another flavivirus such as hepatitis C virus (HCV) or dengue virus (DENV). The antigen from HCV is an antigen including but not limited to HCV capsid protein C, envelope proteins E1 and E2, and nonstructural proteins NS2, NS3, NS4a, NS4b, NS5a and NS5b (C. Wychowski et al. J. Virol 67:1385, 1993) or antigen fragments thereof. In the case of the HCV E2 protein, the sequence may be e.g., as described in QL Choo et al. (PNAS 88:2451-2458, 1991). The antigen from DENV is an antigen including but not limited to envelope (E) protein or antigenic fragments thereof from one or more of the four DENV serotypes.

In another embodiments, the heterologous antigen is a hepatitis B virus surface antigen (HBsAg) with amino acid sequence such as that described by P Charnay et al. (Nucleic Acids Res 7:335-346, 1979) or D. L. Peterson et al (J. Biol. Chem 257:10414-10420, 1982) or HBsAg variants (J. N Zuckerman and A. J Zuckerman, Antiviral Res 60:75-78, 2003).

In another embodiment, the heterologous antigen comprises or consists of an allergen (i.e.: any substance that can cause an allergy), including but not limited to allergens found in animal products (fur and dander; wool, dust mite excretion, etc.); drugs (penicillin, sulfonamides, salicylates, etc.); food (celery, corn, eggs/albumin, fruit, milk/lactose, seafood, sesame, legumes (beans, peas, peanuts, soybeans, etc); soy, tree nuts (pecans, almonds, etc.)); insect stings (bee sting venom, wasp sting venom, mosquito stings, etc.); mold spores, and plant pollens (grass, weeds, ragweed, trees, etc.)

In a further embodiment, the heterologous antigen comprises or consists of other types of disease-related antigens against which it would be beneficial to generate an immune response against, including but not limited to antigens expressed in or on the surface of tumors/tumor cells (including but not limited to p53 (colorectal cancer), alphafetoprotein (germ cell tumors; hepatocellular carcinoma), carcinoembryonic antigen (bowel cancers), CA-125 (ovarian cancer), human epidermal growth factor receptor-2 (HER-2, breast cancer), MUC-1 (breast cancer), NY-ESO-1 (esophageal cancer, non-small-cell lung cancer), epithelial tumor antigen (breast cancer), tyrosinase (malignant melanoma), Disialoganglioside (GD2, neuroblastoma), melanoma-associated antigen gene-1 (MAGE-1 (malignant melanoma)), and beta amyloid (for Alzheimer's and other amyloid-based diseases), etc.

In another embodiment, the composition of any embodiment or combination of embodiments of the invention further comprises an adjuvant. While the examples below demonstrate that adjuvant is not required to induce rapid activation of Ag-specific B cells, leading to significant IgG and IgM production within 7 days, development of both Ab affinity maturation, and immunologic memory, the examples further show that addition of adjuvant to the compositions can result in additional enhancement of the immune response when the compositions are used in the methods of the invention. Any suitable adjuvant can be used, including but not limited to inorganic compounds (aluminum hydroxide, aluminum phosphate, calcium phosphate hydroxide, beryllium, etc.), mineral oil, detergents, cytokines, toll-like receptor agonists, Freund's complete adjuvant, Freund's incomplete adjuvant, squalene, etc. In a preferred embodiment, the adjuvant comprises or consists of a toll-like receptor (TLR) agonist, and more preferably a TLR7 (including but not limited to synthetic small molecule imidazoquinolines, such as imiquimod or resiquimod (R848); CAS number: 144875-48-9; available from InvivoGen) and/or a TLR9 agonist ((including but not limited to Type A, B, or C CpG oligonucleotides; available from InvivoGen). As shown in the examples that follow, use of the compositions of the invention in combination with a TLR7 agonist and/or a TLR9 agonist provide a synergistic induction of the IgG and the IgM responses, enhances the neutralizing Ab response against the WNVE antigen after WNVE-αCD180 conjugate administration, and enhances activation and expansion of the cytotoxic T cell response.

The adjuvant may be present in the composition as an unlinked component, or may be linked to the antigen-CD180 targeting molecule conjugate, depending on the adjuvant and conjugate used. In various non-limiting embodiments, the adjuvant in the composition may comprise flagellins (TLR5 agonists) or nucleic acid agonists of TLR7 and TLR9 that can be synthesized with modified bases allowing linkage to the anti-CD180 (such as via llylamine linkages).

In another embodiment, the compositions of the invention can be modified to extend half-life, such as by attaching at least one molecule to the composition for extending serum half-life, including but not limited to a polyethlyene glycol (PEG) group, serum albumin, transferrin, transferrin receptor or the transferrin-binding portion thereof, or combinations thereof. As used herein, the word "attached" refers to a covalently or noncovalently conjugated substance. The conjugation may be by genetic engineering or by chemical means.

The compositions of the present invention may be stored in any suitable buffer.

In a second aspect, the present invention provides isolated nucleic acids encoding the composition of any embodiment of the first aspect of the invention where the targeting molecule and the antigen are polypeptides. The isolated nucleic acid sequence may comprise RNA or DNA. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals.

In a third aspect, the present invention provides nucleic acid vectors comprising the isolated nucleic acid of the second aspect of the invention. "Recombinant expression vector" includes vectors that operatively link a nucleic acid coding region or gene to any promoter capable of effecting expression of the gene product. The promoter sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, TX). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In a fourth aspect, the present invention provides recombinant host cells comprising the nucleic acid vector of the third aspect of the invention. The host cells can be either prokaryotic or eukaryotic. The cells can be transiently or stably transfected. Such transfection of expression vectors into prokaryotic and eukaryotic cells (including but not limited to Chinese hamster ovary (CHO) cells) can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, NY).

The recombinant host cells can be used, for example in methods for producing antibody (when the targeting molecule is an antibody), comprising:
(a) culturing the recombinant host cell of the invention under conditions suitable for expression of the nucleic-acid encoded antibody composition; and
(b) isolating the antibody composition from the cultured cells.

Suitable conditions for expression of the nucleic-acid encoded antibody composition can be determined by those of skill in the art based on the teachings herein, the specific host cells and vectors used, and the general knowledge of those of skill in the art.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes disclosed herein. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes disclosed herein.

In a fifth aspect, the present invention provides pharmaceutical compositions, comprising:
(a) the composition of embodiment or combination of embodiments disclosed herein; and
(b) a pharmaceutically acceptable carrier.

In this embodiment, the compositions of the invention are present in a pharmaceutical formulation. In this embodiment, the compositions are combined with a pharmaceutically acceptable carrier. Suitable acids which are capable of forming such salts include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming such salts include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

The pharmaceutical composition may comprise in addition to the composition of the invention (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The pharmaceutical compositions of the invention may be made up in any suitable formulation, preferably in formulations suitable for administration by injection. Such pharmaceutical compositions can be used, for example, in methods of use as vaccines, prophylactics, or therapeutics.

The pharmaceutical compositions may contain any other components as deemed appropriate for a given use, such as additional therapeutics or vaccine components. In one embodiment, the pharmaceutical compositions further comprise toll-like receptor agonists including but not limited to Ribi, a TLR7 agonist (including but not limited to R848) and/or a TLR9 agonist ((including but not limited to Type A, B, or C CpG oligonucleotides).

In a sixth aspect, the present invention provides methods for treating or limiting development of a disorder, comprising administering to an individual at risk of a disorder an amount effective to treat or limit development of the disorder of the composition or pharmaceutical composition, or a pharmaceutical salt thereof, of any embodiment or combination of embodiments of the present invention. In one embodiment, the compositions are used prophylactically as vaccines to limit infectious disease/severity of infectious disease, such as in individuals that have not been exposed to an infectious agent but are at risk of such exposure. In other embodiments, the compositions can be used therapeutically to treat people exposed to or chronically infected with a pathogen. In a further embodiment, the compositions are used as cancer vaccines, to treat an individual with a tumor. As will be understood by those of skill in the art, the specific antigen/composition to be used will depend on the specific disorder to be treating or limited.

Suitable acids which are capable of forming pharmaceutically acceptable salts include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming pharmaceutically acceptable salts include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

The methods of the invention target antigen to CD180, a surface protein expressed on B cells, macrophages, and dendritic cells, that to produce antigen-specific IgG in the absence of T cell costimulation (such as CD40 deficiency) or the complete absence of T cells (such as TCR B/8 deficiency). Thus, the methods can be used in any therapeutic or prophylactic treatment for which a suitable antigen is available. As shown in the examples that follow, induction of antigen specific IgG and IgM by anti-CD180 conjugates is rapid (within 7 days as opposed to 14+ days for most conventional immunization systems) and requires no additional inflammation-inducing adjuvant. Remarkably, a single injection of Ag-CD180 antibody (αCD180) without any additional adjuvant also led to the development of both antibody (Ab) affinity maturation and immunologic memory. Furthermore, as shown in the examples that follow, mice inoculated with a CD180 targeting molecule to which purified recombinant West Nile virus (WNV) envelope (E) protein has been attached (WNVE) develop both WNVE specific IgG Abs and neutralizing Abs to WNVE, and that mice immunized with WNVE-CD180 conjugates are protected from death induced by intracranial challenge with WNV. These data are merely exemplary of how the methods of the present invention can be used to treat or limit development of a disease.

Thus, the approach of targeting antigen to CD180 results in both significant advantages compared to traditional (e.g. IM antigen in alum) immunization approaches and allows for vaccination of previously untreatable populations. This approach also finds use, for example, for neonates, the elderly, and the immunodeficient, both in specifically targeting cellular populations enriched in underdeveloped or otherwise deficient immune systems and by improving responses to antigens that require linked recognition (carbohydrate epitopes, etc.).

As used herein, "treat" or "treating" means accomplishing one or more of the following in an individual that already has a disorder or has already been exposed to a disorder-causing substance/pathogen: (a) reducing the severity of the disorder; (b) limiting or preventing development of symptoms characteristic of the disorder(s) being treated (ex: immune deficiencies in cancer patients or other patients) undergoing chemotherapy and/or radiation therapy); (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "limiting" or "limiting development of" means accomplishing one or more of the following in an individual that does not have the disorder to be limited: (a) preventing the disorder; (b) reducing the severity of the disorder; and (c) limiting or preventing development of symptoms characteristic of the disorder.

As used herein, an "amount effective" refers to an amount of the composition that is effective for treating and/or limiting the relevant disorder.

While the examples below demonstrate that adjuvant is not required to induce rapid activation of Ag-specific B cells, leading to significant IgG and IgM production within 7 days, development of both Ab affinity maturation, and immunologic memory, the examples further show that addition of adjuvant to the compositions can result in additional enhancement of the immune response when the compositions are used in the methods of the invention. Thus, in a further embodiment, the methods may further comprise administering an adjuvant to the individual. Any suitable adjuvant can be used, including but not limited to inorganic compounds (aluminum hydroxide, aluminum phosphate, calcium phosphate hydroxide, beryllium, etc.), mineral oil, detergents, cytokines, toll-like receptor agonists, Freund's complete adjuvant, Freund's incomplete adjuvant, squalene, etc. In a preferred embodiment, the adjuvant comprises or consists of adjuvant comprises or consists of a toll-like receptor (TLR) agonist, and more preferably a TLR7 (including but not limited to synthetic small molecule imidazoquinolines, such as imiquimod or resiquimod (R848); CAS number: 144875-48-9; available from InvivoGen) and/or a TLR9 agonist ((including but not limited to Type A, B, or C CpG oligonucleotides; available from InvivoGen). As shown in the examples that follow, use of the compositions of the invention in combination with a TLR7 agonist and/or a TLR9 agonist provide a synergistic induction of the IgG and the IgM responses, enhances the neutralizing Ab response against the WNVE antigen after WNVE-αCD180 conjugate administration, and enhances activation and expansion of a CD4 T cell response or a cytotoxic T cell response.

The individual may be any suitable individual, including but not limited to mammals. Preferably the individual is a human. In one embodiment, the individual has a T-cell deficiency and/or a defect in co-stimulation between B cells and T cells, or is immuno-compromised by chronic infections or from acute or chronic taking of immunosuppressive drugs for treatment of autoimmune diseases, or other inflammatory disease. In another embodiment, the individual is a neonate or is elderly (i.e.: at least 65 years old).

In various other embodiments, the individual has an allergy, has a congenital or acquired immunodeficiency, or has been exposed to an infectious agent.

In various further embodiments, the individual suffers from one or more of ataxia-telangiectasia, hyper-IgM syndrome, DiGeorge Syndrome, Wiscott-Aldrich Syndrome, Common Variable Immunodeficiency Syndromes, Polysaccharide response defects including Selective Antibody Deficiency with Normal Immunoglobulins (SADNI), viral infection, cancer, hepatitis, diabetes, and immunosuppression following bone marrow or organ transplants or cytotoxic/myeloablative therapy. or is a pregnant female, asplenic, taking drugs that cause myelosuppression or reduction in lymphocytes (including but not limited to corticosteroids, cyclosporine, amphotericin B, chloramphenicol, various cancer chemotherapeutics, gold compounds, methotrexate, etc.), receiving radiation therapy, and/or has chronic renal failure.

As will be understood by those of skill in the art, the methods can be used to treat or limit development of any disorder mediated by a pathogen or allergen for which an appropriate antigen can be provided in the composition, including but not limited to hepatitis (A, B, C, E, etc.) virus, human papillomavirus, herpes simplex viruses, cytomegalovirus, Epstein-Barr virus, influenza virus, parainfluenza virus, enterovirus, measles virus, mumps virus, polio virus, rabies virus, human immunodeficiency virus, respiratory syncytial virus, Rotavirus, rubella virus, varicella zoster virus, Ebola virus, cytomegalovirus, Marburg virus, norovirus, variola virus, any Flavivus including but not limited to West Nile virus, yellow fever virus, dengue virus, tick-borne encephalitis virus, and Japanese encephalitis virus; human immunodeficiency virus (HIV), *Bacillus anthracis, Bordetalla pertusis, Chlamydia trachomatis, Clostridium tetani, Clastridium difficile, Corynebacterium diptheriae, Coxiella burnetii, Escherichia coli, Haemophilus influenza, Helicobacter pylori, Leishmania donovani, L. tropica* and *L. braziliensis, Mycobacterium tuberculosis, Mycobacterium leprae, Neisseria meningitis, Plasmodium falciparum, P. ovale, P. malariae* and *P. vivax, Pseudomonas aeruginosa, Salmonella typhi, Schistosoma hematobium, S. mansoni, Streptococcus pneumoniae* (group A and B), *Staphylococcus aureus, Toxoplasma gondii, Trypanosoma brucei, T. cruzi* and *Vibrio cholerae*; allergens found in animal products (fur and dander; wool, dust mite excretion, etc.); drugs (penicillin, sulfonamides, salicylates, etc.); food (celery, corn, eggs/albumin, fruit, milk/lactose, seafood, sesame, legumes (beans, peas, peanuts, soybeans, etc); soy, tree nuts (pecans, almonds, etc.)); insect stings (bee sting venom, wasp sting venom, mosquito stings, etc.); mold spores, plant pollens (grass, weeds, ragweed, trees, etc; antigens expressed in or on the surface of tumors/tumor cells (including but not limited to p53 (colorectal cancer), alphafetoprotein (germ cell tumors; hepatocellular carcinoma), carcinoembryonic antigen (bowel cancers), CA-125 (ovarian cancer), human epidermal growth factor receptor-2 (HER-2, breast cancer), MUC-1 (breast cancer), NY-ESO-1 (esophageal cancer, non-small-cell lung cancer), epithelial tumor antigen (breast cancer), tyrosinase (malignant melanoma), Disialoganglioside (GD2, neuroblastoma), melanoma-associated antigen gene-1 (MAGE-1 (malignant melanoma)), and beta amyloid (for Alzheimer's and other amyloid-based diseases), etc.

Thus, the methods can be used, for example, to treat or limit development of any disorders associated with the antigens listed above (i.e. relevant viral and bacterial infections, chickenpox, cervical cancer, genital warts, gastroenteritis, smallpox, anthrax, whooping cough, tetanus, diphtheria, meningitis, viral encephalitis, malaria, diarrhea, pneumonia, acquired immune deficiency syndrome, tuberculosis, cholera, typhoid fever, cancer, Alzheimer's disease, etc.).

In one non-limiting embodiment, the method is used to treat or limit development of disease caused by West Nile virus (WNV) infection. In this embodiment, the heterologous antigen is an antigen from West Nile virus (WNV), including but not limited to including but not limited to WNV envelope protein E with an amino acid sequence similar to or identical to those described (T. J Chambers et al., *J General Virology* 79:2375-2380, 1998) or antigenic fragments thereof. or a WNV nonstructural (NS) protein such as NS2a, NS2b, NS3, NS4a, NS4b or NS5. or antigenic fragments thereof. As shown in the examples that follow, mice inoculated with a CD180 targeting molecule to which purified recombinant West Nile virus (WNV) envelope (E) protein has been attached (WNVE) develop both WNVE specific IgG Abs and neutralizing Abs to WNVE, and that mice immunized with WNVE-CD180 conjugates are protected from death induced by intracranial challenge with WNV. These data are merely exemplary of how the methods of the invention can be used to treat or limit development of a disorder for which an appropriate antigen is available for generating an immune response against.

Symptoms characteristic of disease caused by WNV include, but are not limited to headache, fever, rash, neuroinvasive disease, encephalitis, meningitis, meningioencephalitis, and poliomyelitis. Thus, the methods of the invention may serve, for example, to therapeutically treat or limit development of these symptoms and/or to limit WNV replication in someone exposed to WNV prior to the methods, or to prophylactically limit development of these symptoms and/or to limit WNV replication in someone exposed top WNV only after the methods of the invention.

In another embodiment, the method is used to treat or limit development of disease caused by another flavivirus such as hepatitis C virus (HCV) or dengue virus (DENV). In this embodiment, the heterologous antigen from HCV can be an antigen including but not limited to HCV capsid protein C, envelope proteins E1 and E2, and nonstructural proteins NS2, NS3, NS4a, NS4b, NS5a and NS5b (C. Wychowski et al. J. Virol 67:1385, 1993) or antigen fragments thereof. In the case of the HCV E2 protein, the sequence may be e.g., as described in QL Choo et al. (PNAS 88:2451-2458, 1991). The antigen from DENV can be an antigen including but not limited to envelope (E) protein or antigenic fragments thereof from one or more of the four DENV serotypes.

In another embodiment, the method is used to treat or limit development of disease caused by a hepatitis B virus, where the antigen may be, for example, surface antigen (HBsAg) with amino acid sequence such as that described by P Charnay et al. (Nucleic Acids Res 7:335-346, 1979) or D. L. Peterson et al (J. Biol. Chem 257:10414-10420, 1982) or HBsAg variants (J. N Zuckerman and A. J Zuckerman, Antiviral Res 60:75-78, 2003).

The compositions are typically formulated as a pharmaceutical composition, such as those disclosed above, and can be administered via any suitable route, including orally, parenterally, by inhalation spray, rectally, or topically in dosage unit formulations containing conventional pharmaceutically acceptable carriers, adjuvants, and vehicles. Preferably, the compositions are administered parenterally. The term parenteral as used herein includes, subcutaneous, intravenous, intra-arterial, intramuscular, intrasternal, intratendinous, intraspinal, intracranial, intrathoracic, infusion techniques or intraperitoneally. Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The compositions can be delivered in a single bolus, or may be administered more than once (e.g., 2, 3, 4, 5, or more times) as determined by an attending physician.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number, respectively. Additionally, the words "herein," "above," and "below" and words of similar import, when used in this application, shall refer to this application as a whole and not to any particular portions of this application. As used herein, the singular forms "a", "an" and "the" include plural referents unless the context clearly dictates otherwise. "And" as used herein is interchangeably used with "or" unless expressly stated otherwise.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments.

All of the references cited herein are incorporated by reference. Aspects of the disclosure can be modified, if necessary, to employ the compositions, functions and concepts of the above references and application to provide yet further embodiments of the disclosure. These and other changes can be made to the disclosure in light of the detailed description.

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

Example: Targeting Antigens to CD180 Rapidly Induces Antigen-Specific IgG, Affinity Maturation and Immunologic Memory Summary Here we report that targeting antigen (Ag) to a receptor expressed on both B cells and dendritic cells (DCs), the TLR orphan receptor CD180, in the absence of adjuvant rapidly induced IgG responses that were stronger than those induced by Ag in alum. Ag conjugated to anti-CD180 (Ag-αCD180) induced affinity maturation and antibody (Ab) responses that were partially T cell-independent, as Ag-specific IgG were generated in CD40- and T cell-deficient mice. After pre-immunization with Ag-αCD180 and boosting with soluble Ag both WT and CD40 KO mice rapidly produced Ag-specific IgG forming cells, demonstrating that Ag-anti-CD180 induces immunologic memory. The potent adjuvant effect of Ag-αCD180 required Ag to be coupled to anti-CD180 and the responsive B cells to express both CD180 and an Ag-specific B cell receptor (BCR). Surprisingly, CD180 Ag-targeting also induced IgG Abs in BAFF-R KO mice lacking mature B cells and in mice deficient in interferon-signaling. Targeting Ag to CD180 is thus useful for therapeutic vaccination and for vaccinating the immune-compromised.

Results

Targeting Antigen to CD180 Rapidly Induces Strong Ag-Specific IgG Responses

Figure 1A:
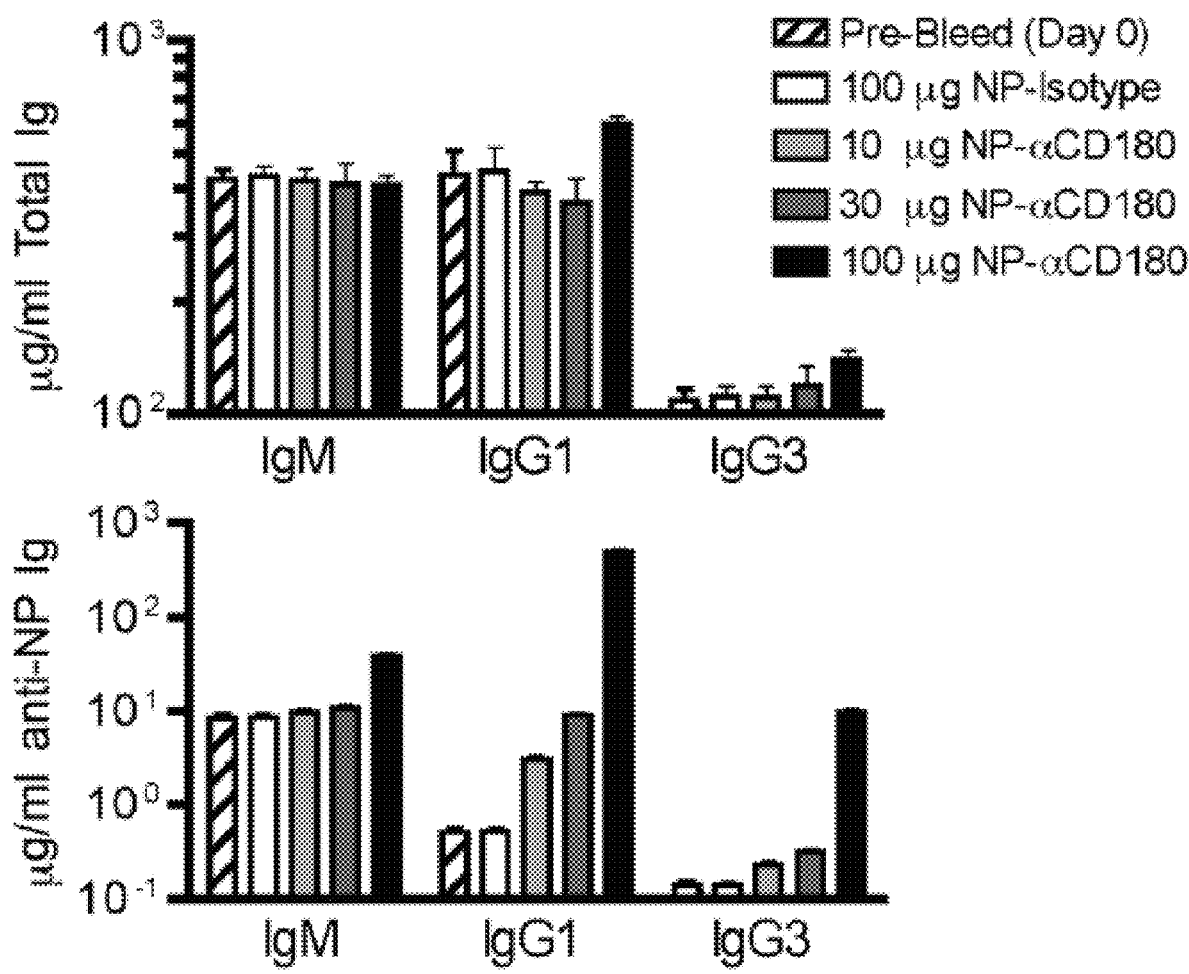
FIG. 1A-1C. Targeting to CD180 induces Ag-specific IgG production that is partially T cellindependent. (A) WT mice were inoculated i.v. with either 100 μg of NP-isotype control mAb (white bars) or graded doses of NP-αCD180 mAb (10, 30 or 100 μg, light grey, medium grey and black bars respectively); mice were pre-bled at d 0 (100 μg NP-αCD180 group only, hatched bars) or d 10 and total serum Ig (top) or anti-NP specific (bottom) IgM, IgG1 and IgG3 levels determined by ELISA. (B) WT, CD40 KO, or TCR KO mice were inoculated with 100 μg NP-αCD180 mAb (black) or NP-isotype mAb (white) or αCD180 (hatched), bled at d 10, and analyzed for NP-specific IgM, IgG1 and IgG3 responses. (C) WT or CD40 KO mice were treated as in (B), bled at d 0 and d 10, and sera analyzed for levels of NP-specific Abs (IgM and IgG subclasses). Data are representative of 3 experiments (A), 4 experiments (B), and 3 experiments (C) using 3 mice/group.

We examined whether Ag coupled to anti-CD180 could induce Ag-specific IgG responses in normal and immuno-deficient mice. We first conjugated the hapten (4-hydroxy-3-nitrophenyl)acetyl (NP) to anti-CD180 (NP-αCD180) or to a non-binding rat IgG2a isotype control (NP-isotype) mAb and administered them in graded doses i.v. to WT mice. Doses ranging from 10- to 100 μg of NP-αCD180 induced significant NP-specific IgG responses in a dose dependent manner (FIG. 1A, bottom) with little or no polyclonal Ig production compared to unimmunized mice (pre-bleed for 100 μg NP-αCD180 group) or mice injected with 100 μg NP-isotype (FIG. 1A, top). Anti-NP Abs were not observed in mice immunized with anti-CD180 mAb alone (FIG. 1 B); therefore, the Ag-specific Ab response to NP-αCD180 was due to targeting of Ag rather than from a product of polyclonal Ig production. Strong Ag-specific Ab response to NP-αCD180 were also induced when conjugates were inoculated i.p. (data not shown); in subsequent studies we inoculated mice via the i.v. route.

Figure 1B:
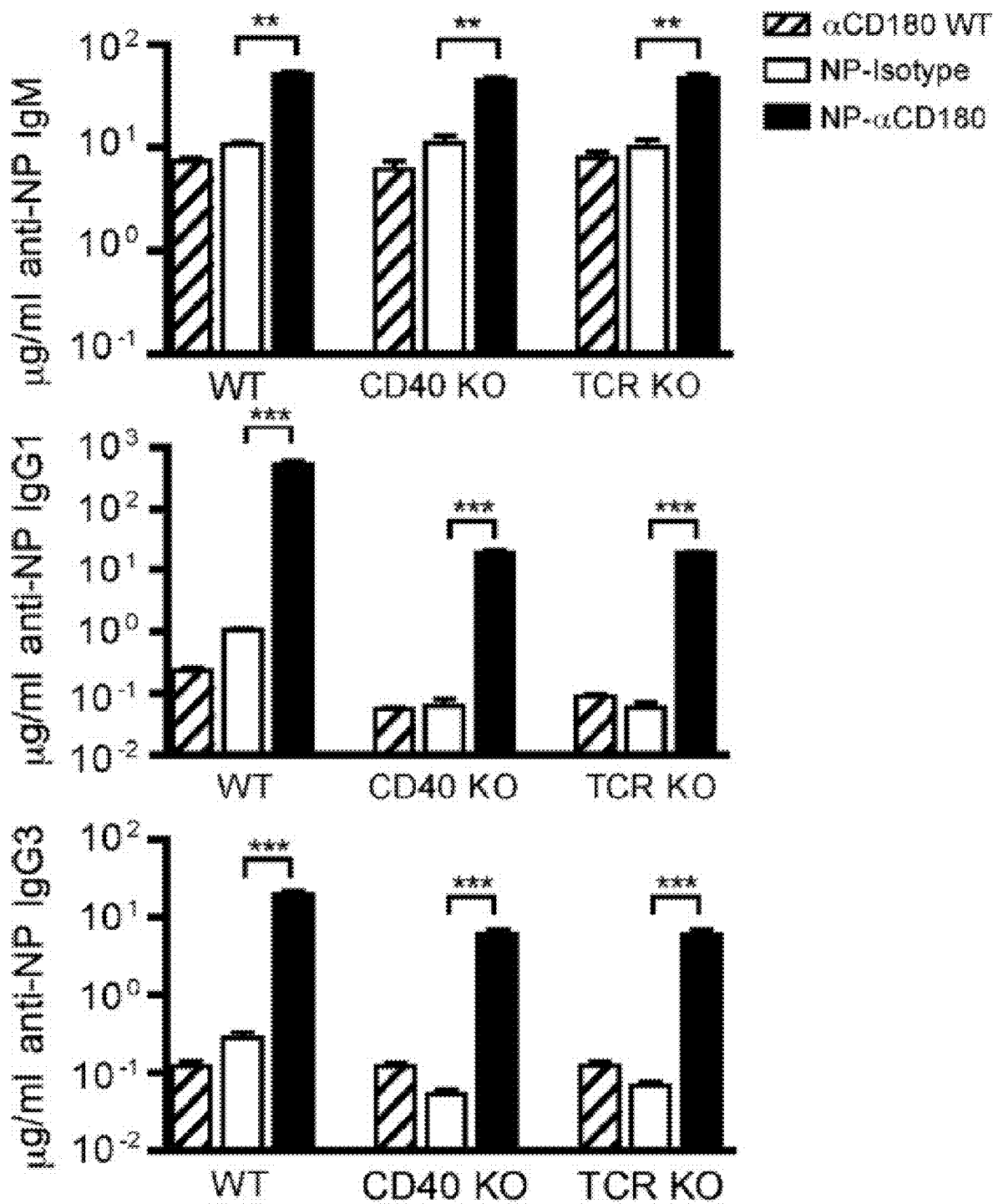
Figure 1C:
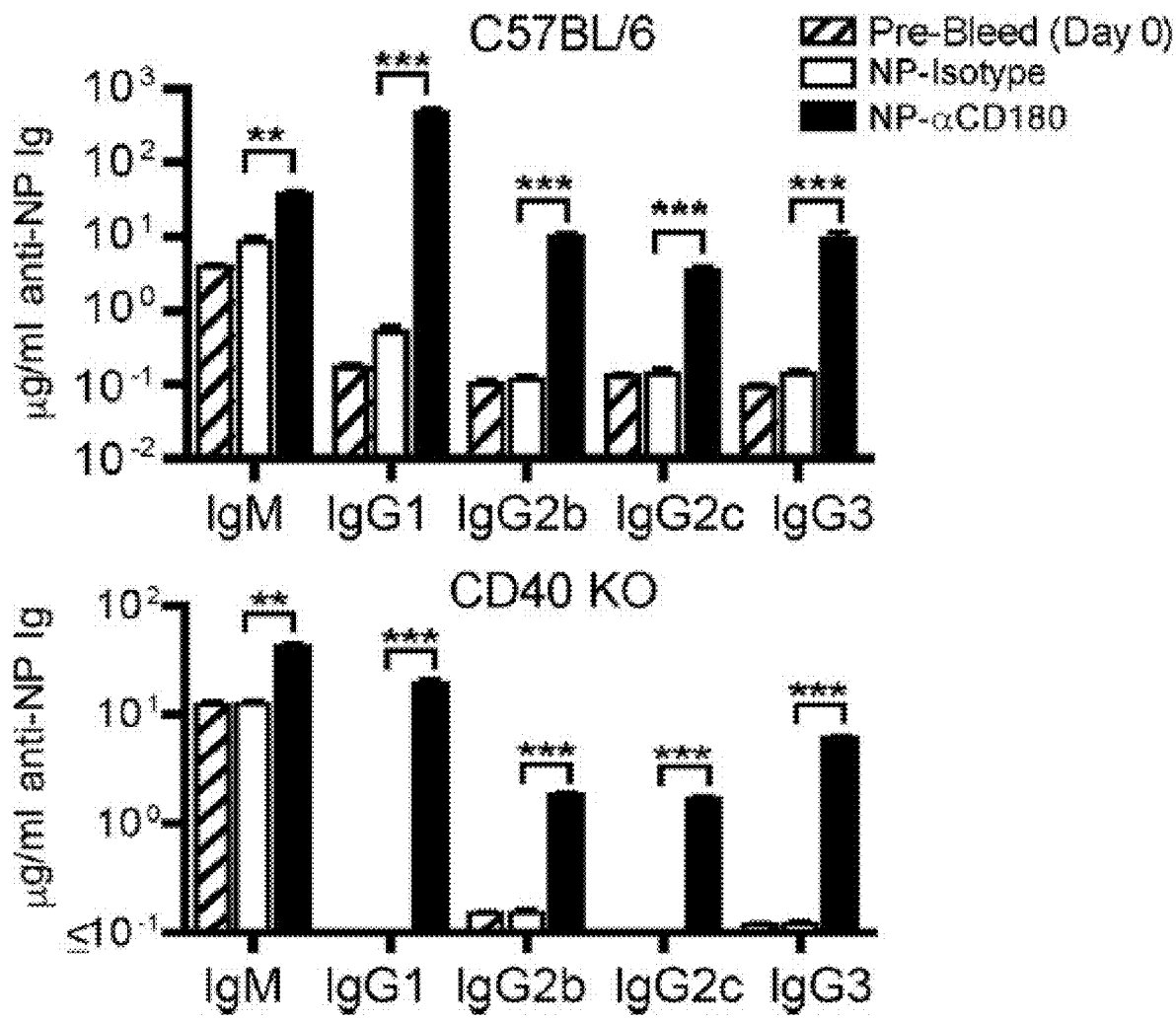

Targeting Ag to CD180 also induced Ag-specific IgM and IgG production in both CD40 KO mice and T cell deficient (TCRβ/δ KO) mice (FIG. 1 B). Ag-specific IgM levels were similar in the WT and immunodeficient mice, but Ag-specific IgG levels were significantly lower in both CD40

KO and TCRβ/δ KO mice. Despite the overall reduction in Ag-specific IgG in immunodeficient mice, the broad IgG subclass distribution was maintained and similar to that in WT mice (FIG. 1 C). In addition to Ag-specific IgG, NP-αCD180 also induced Ag-specific IgA Abs, but not IgE Abs (data not shown). We conclude that targeting Ag to CD180 induces both TD and TI IgG antibody responses.

Figure 2A:
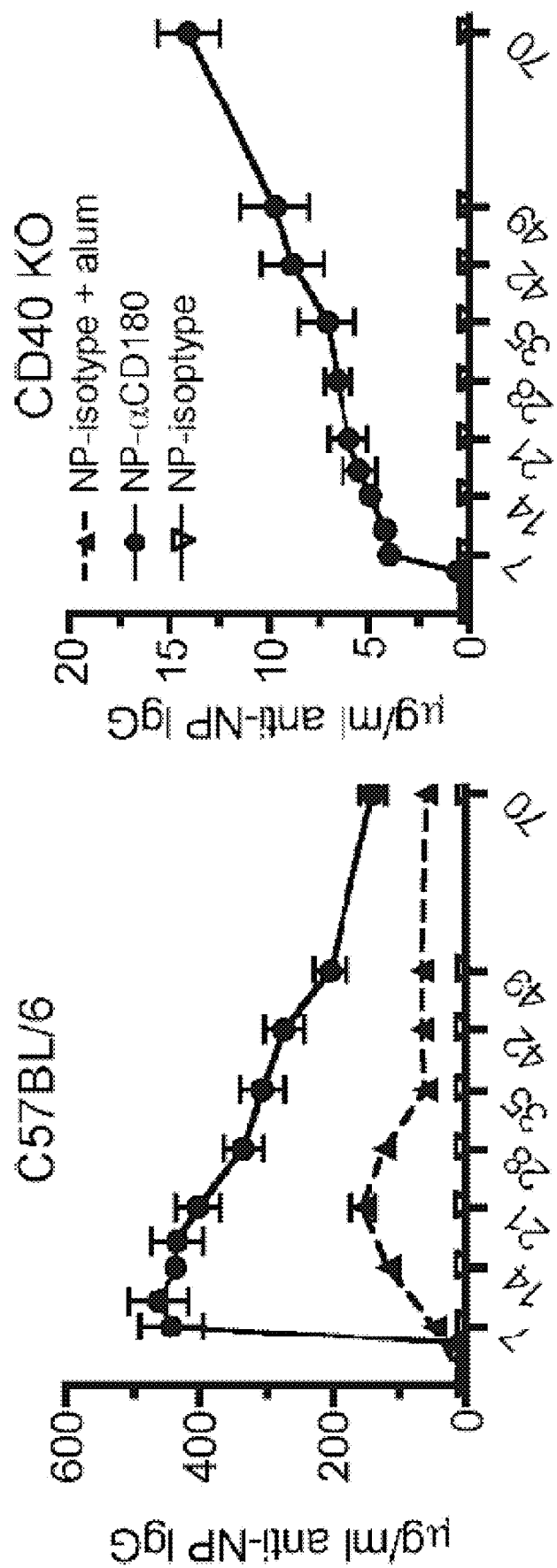
FIG. 2A-2C. CD180 targeting rapidly induces higher levels of Ag-specific IgG than Ag in alum. (A) WT or CD40 KO mice were inoculated i.v. with either 100 μg NP-αCD180 (circles) or NP-isotype (upside down triangles) or i.p. with 100 μg NP-isotype in alum (triangles), bled at the indicated time points and serum analyzed for levels of NP-specific IgG. (B) WT mice were inoculated i.v. with either 100 μg OVA-αCD180 or OVA-isotype, or i.p. with 100 μg OVA-isotype in alum, bled at day 7 p.i. and serum analyzed for levels of OVA-specific IgG. (C) WT mice were inoculated with 100 μg each of the indicated stimuli and bled on d 10 and evaluated for levels of NP specific IgG (white columns) or OVA-specific IgG (black columns). Three mice/group, data representative of 2 experiments (A), or 3 experiments (B, C).
Figure 2B:
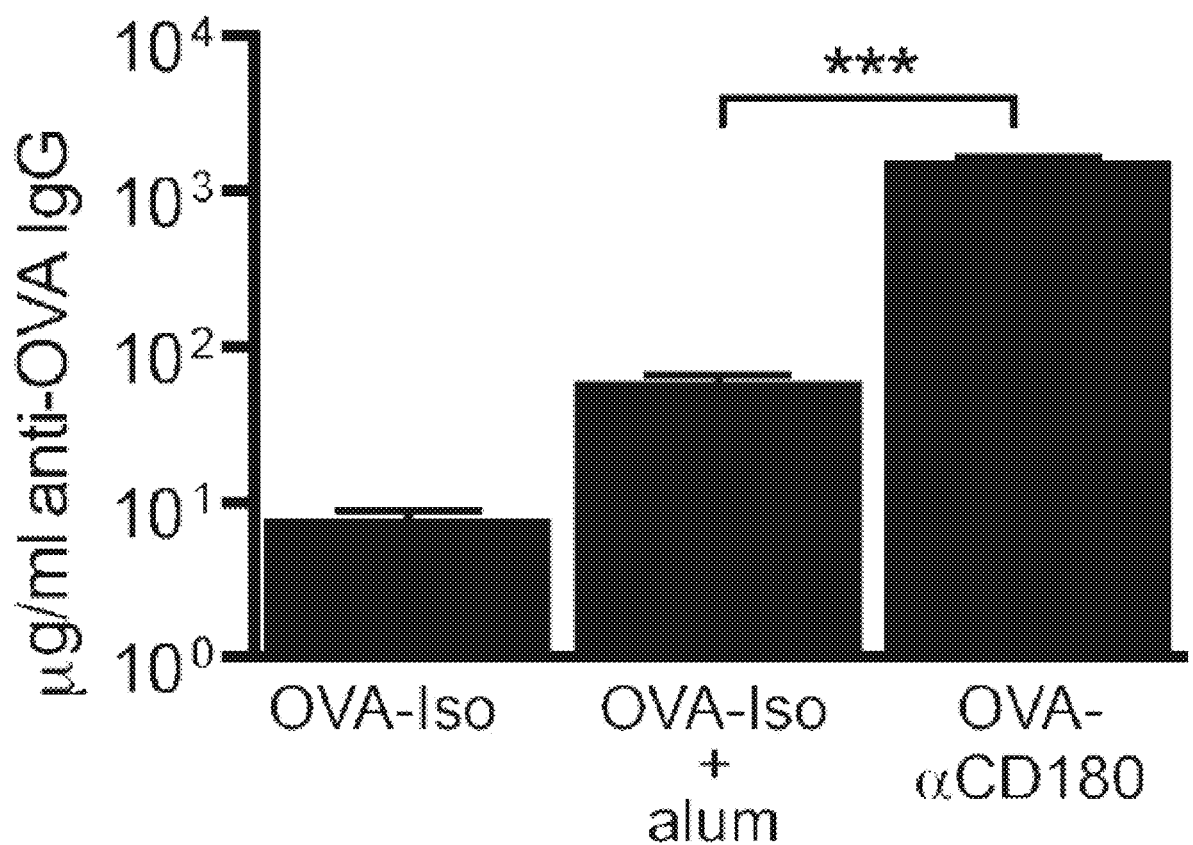
Figure 2C:
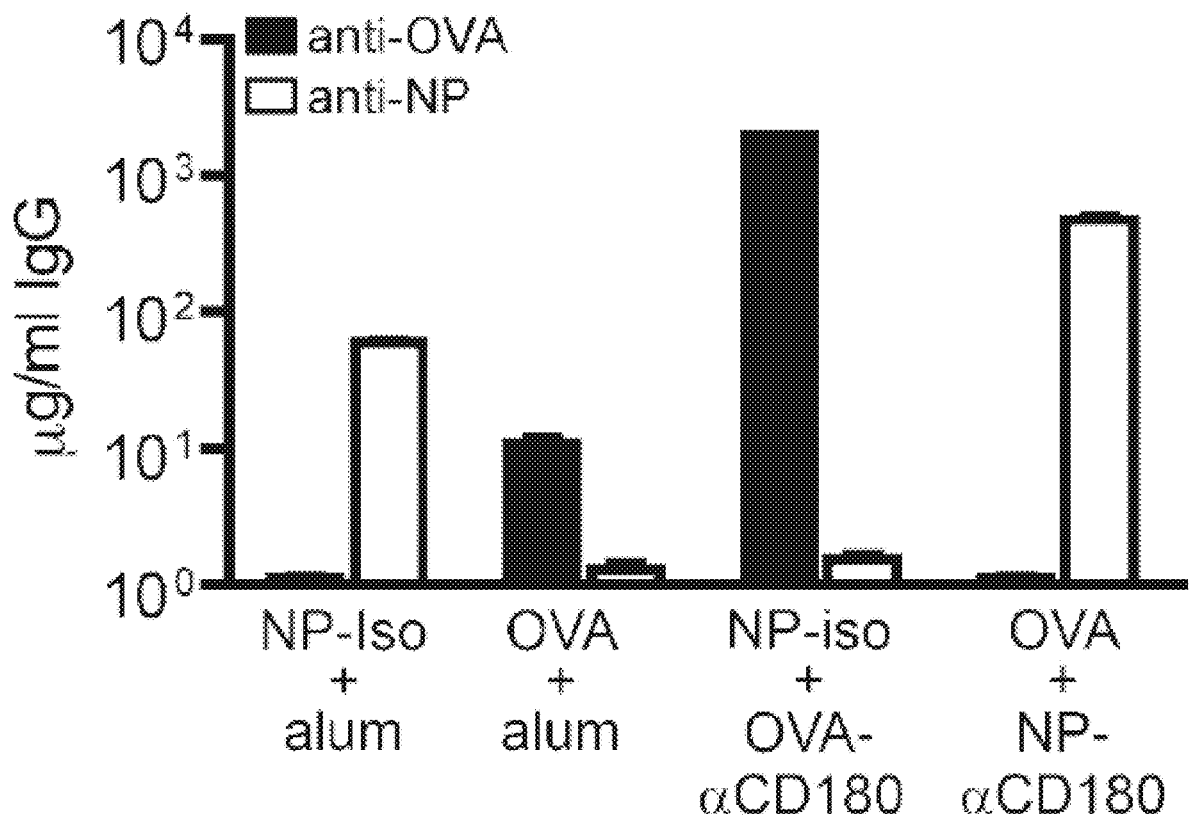

CD180 targeting rapidly induces higher levels of Ag-specific IgG than Ag inoculated in alum We next determined the kinetics of Ag-specific IgG production following NP-αCD180 inoculation. We immunized WT or CD40 KO mice i.v. with either NP-αCD180 or NP-isotype, or i.p. with the NP-isotype Ag precipitated in alum. In WT mice, NP-αCD180 induced a rapid anti-NP IgG response that peaked 10 d p.i. as compared to Ag in alum, which peaked on d 21. Mice inoculated with NP-isotype alone did not produce more than 2 µg/mL of anti-NP Ab at any time point (FIG. 2A, left). As expected, CD40 KO mice immunized with Ag in alum did not make an NP-specific IgG response; however, they did develop a significant and continually increasing amount of NP-specific IgG after CD180 targeting (FIG. 2 A, right).

Targeting to CD180 Induces Anti-Protein IgG Responses and Requires Covalently Linked Ag We next determined whether the strong Ab response to NP-αCD180 was also induced when we targeted protein antigens to CD180. We coupled whole OVA to anti-CD180 (OVA-αCD180) and isotype mAb (OVA-isotype) and immunized WT mice i.v. with one of these antigens or i.p. with OVA-isotype in alum (FIG. 2 B). As with NP-αCD180, OVA-αCD180 induced a strong Ag-specific IgG response with concentrations of nearly 2 mg/ml of IgG anti-OVA at day 14 p.i.

Anti-CD180 alone can stimulate B cells and thus has the potential to convert B cells into efficient antigen presenting cells (APCs) so they could present Ag even if it were administered in an unlinked fashion. To test this possibility, we inoculated mice with two different Ags with only one Ag coupled to αCD180: NP-αCD180+soluble OVA or OVA-αCD180+soluble NP-isotype. As expected, mice inoculated with only NP-isotype in alum or OVA in alum produced IgG only against NP or OVA, respectively (FIG. 2 C). Mice inoculated with NP or OVA coupled to anti-CD180 together with soluble OVA or soluble NP-isotype only made Abs against the Ag coupled to anti-CD 180 and not to the soluble, unlinked Ag. We conclude that during Ag targeting to CD180, only B cells specific for the Ag attached to anti-CD180 are driven to produce Ab.

Figure 3A:
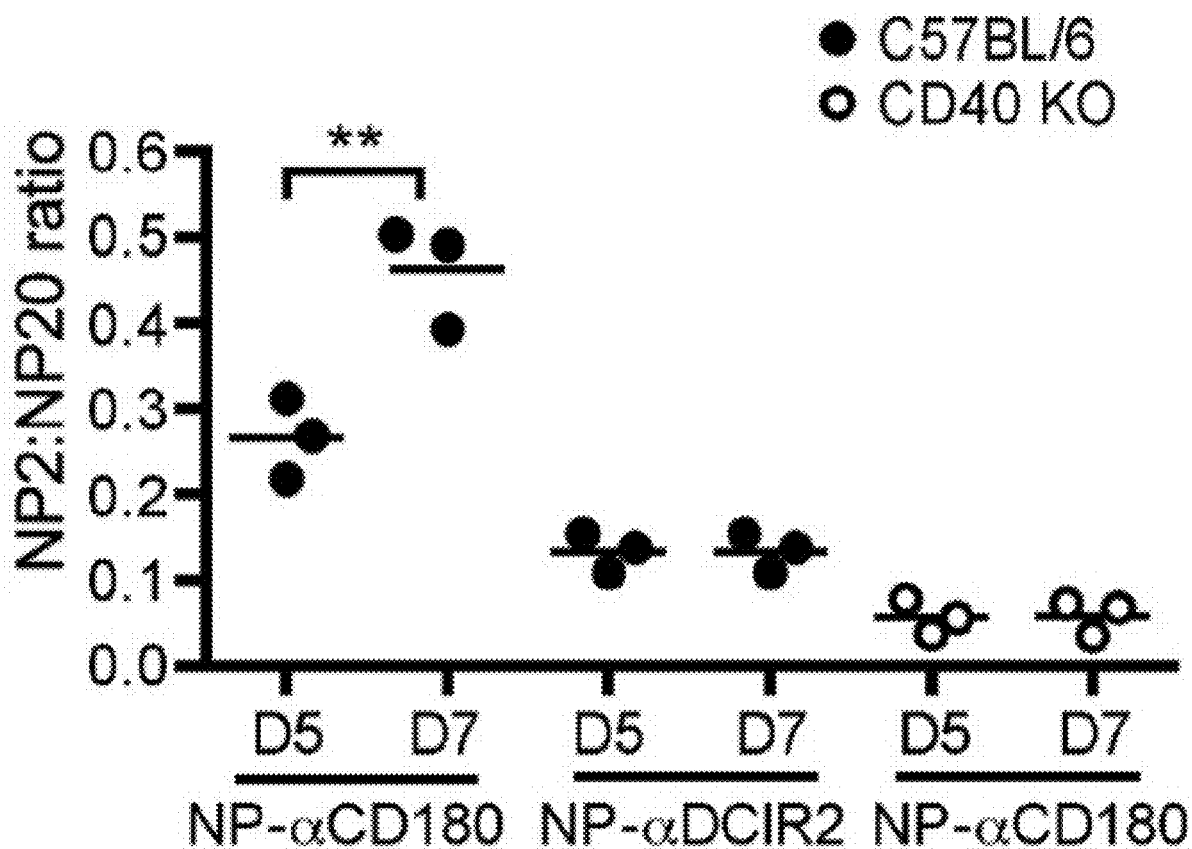
FIG. 3A-3I. CD180 targeting induces affinity maturation, EF responses, germinal center formation and immunologic memory. (A) Sera from WT (black circles) or CD40 KO mice (open circles) immunized with 100 μg NP-αCD180 or 10 μg NP-αDCIR2 were analyzed for affinity to NP on days 5 and 7 p.i. (B) WT (black circles) were inoculated with 100 μg NP-αCD180 alone or with the indicated adjuvant (50 μg CpG-A, 50 μg CpG-B, 20 μg R848, or 4 μg LPS) then bled at d 7 and d 28; sera were analyzed for affinity against NP. Controls included mice inoculated with NP iso, NP-iso+ alum or NP-αDCIR2. (C) WT mice were inoculated with 50 μg NP-αCD180 alone or with the indicated adjuvants as in (B) and bled at d 7, 14, 21 and 28; sera were analyzed for levels of NP-specific IgM (left) or IgG (right) Abs. A representative experiment of three experiments each for A, B, and C is shown. (D-F) 2×105 NP-binding B cells from Ly5.1+ B1-8hi mice were adoptively transferred to Ly5.2+ WT recipients on d-1. On d 0 the mice were inoculated with 100 μg of either NP-αCD180 (black) or NP-isotype (white) and spleens harvested at either d 4 or d 7 for flow cytometric analysis. The number of NP-specific B220+ B cells (D) and NP-specific PNA+GL7+GC B cells (E) per spleen were determined by sequential gating on Ly5.1+NP-binding B cells. (F) The number of B220loCD138+ AFCs per spleen are plotted. Data representative of two experiments for D-F. (G) 8 μM frozen spleen sections from mice immunized with NP-CGG+ alum or NP-αCD180 either 4 or 7 days previously were stained with anti-B220-eFluor450, PNA-FITC, and NP-PE. Data are representative of multiple sections analyzed from 2-3 mice per time point. Scale bars represent 100 μM. (H) Mean number of PNA+ GCs per follicle from mice in (G) (day 7 time point). Each dot represents one animal from which 4 individual sections were analyzed. Data in G and H depict a representative experiment of 2 independent experiments. (I) WT and CD40 KO mice were primed as indicated, rested for 10 wks, then given a secondary challenge i.p. with Ag (20 μg) or PBS. Spleens were harvested d 4 post-boost and analyzed for NP-specific AFC by ELISPOT. The combined results from two independent experiments using 3 mice/group are shown. Each dot represents an individual animal. Statistical values compare groups to mice primed with NP-αCD180 and challenged with NP-isotype. * $p<0.05$;  $p<0.01$; * $p<0.001$.
Figure 3B:
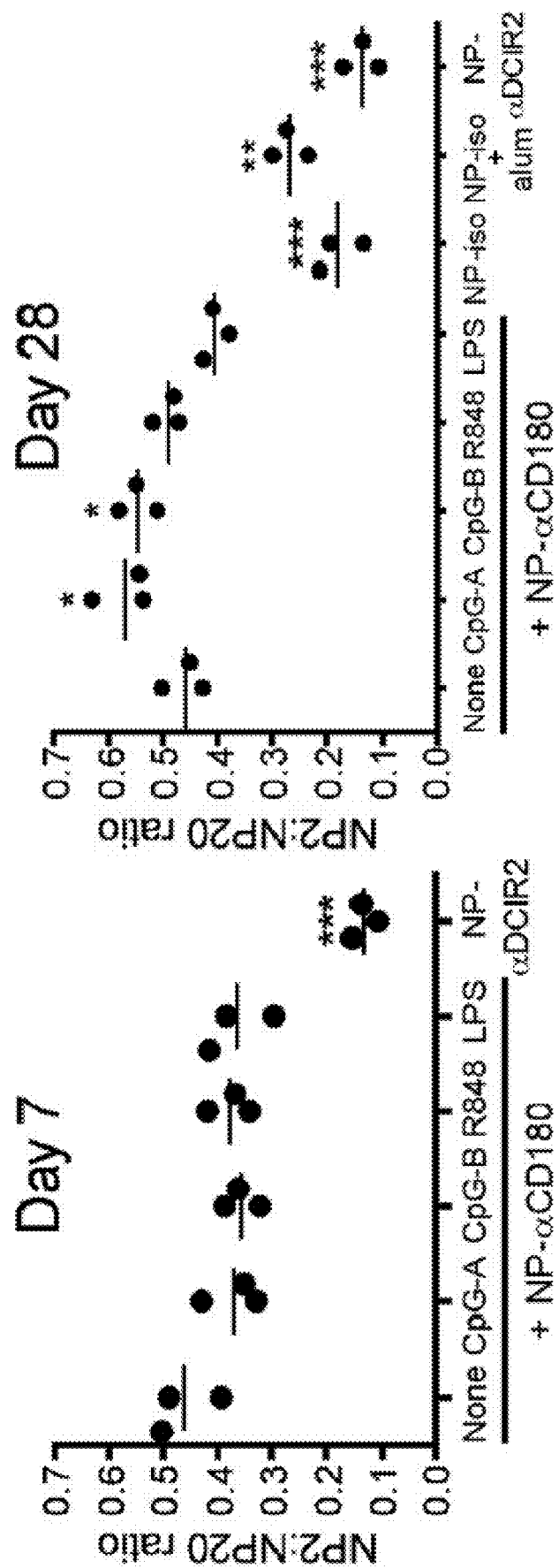
Figure 3C:
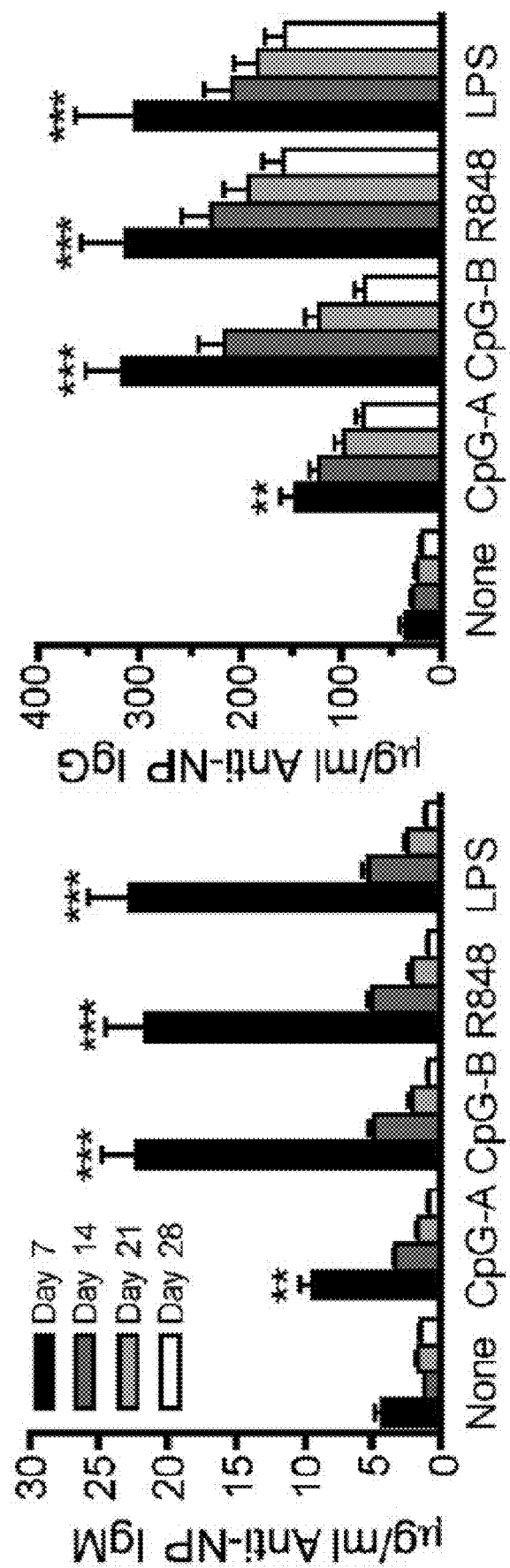
Figure 3D:
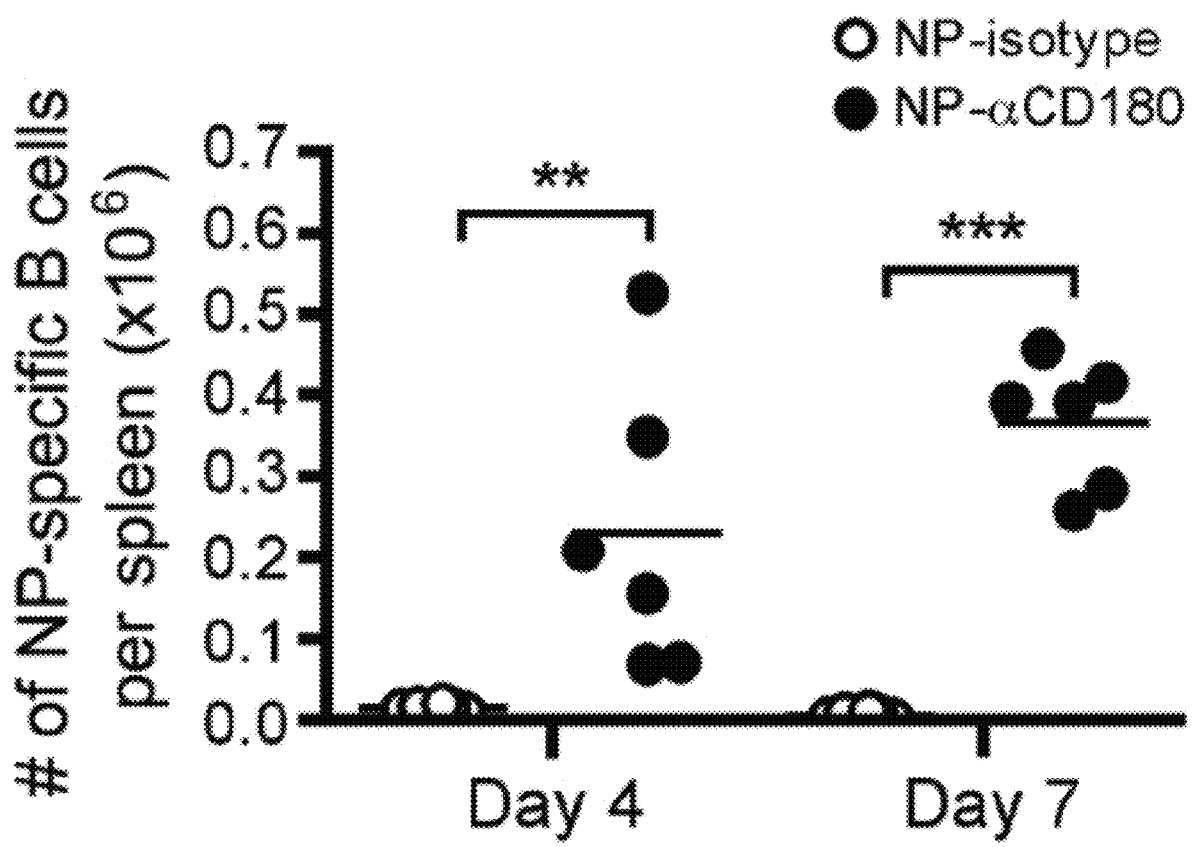
Figure 3E:
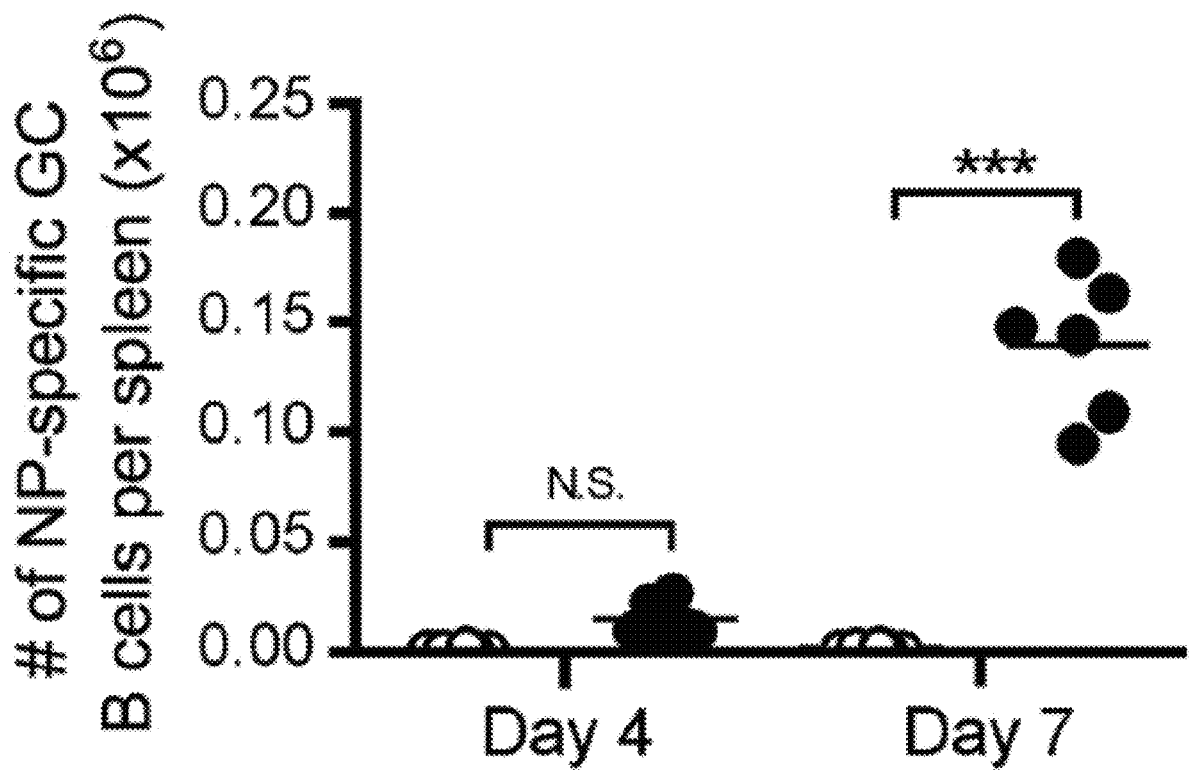
Figure 3F:
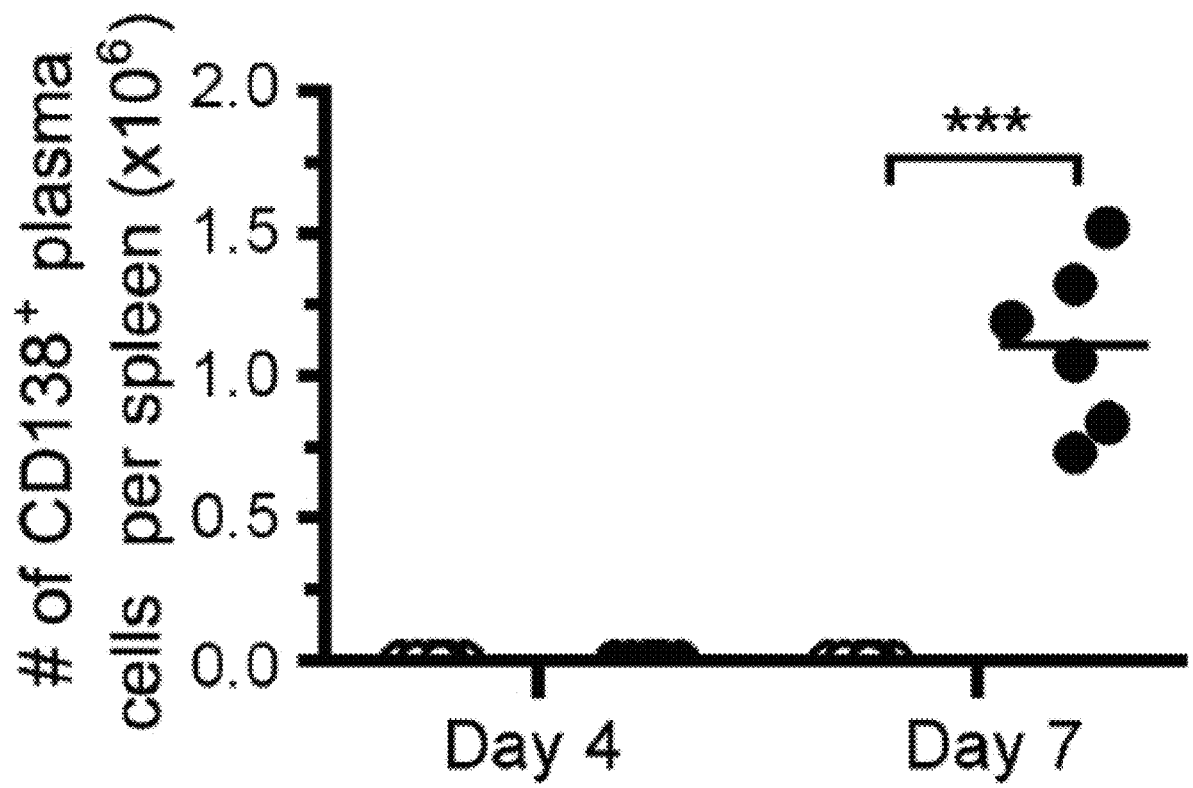
Figure 3G:
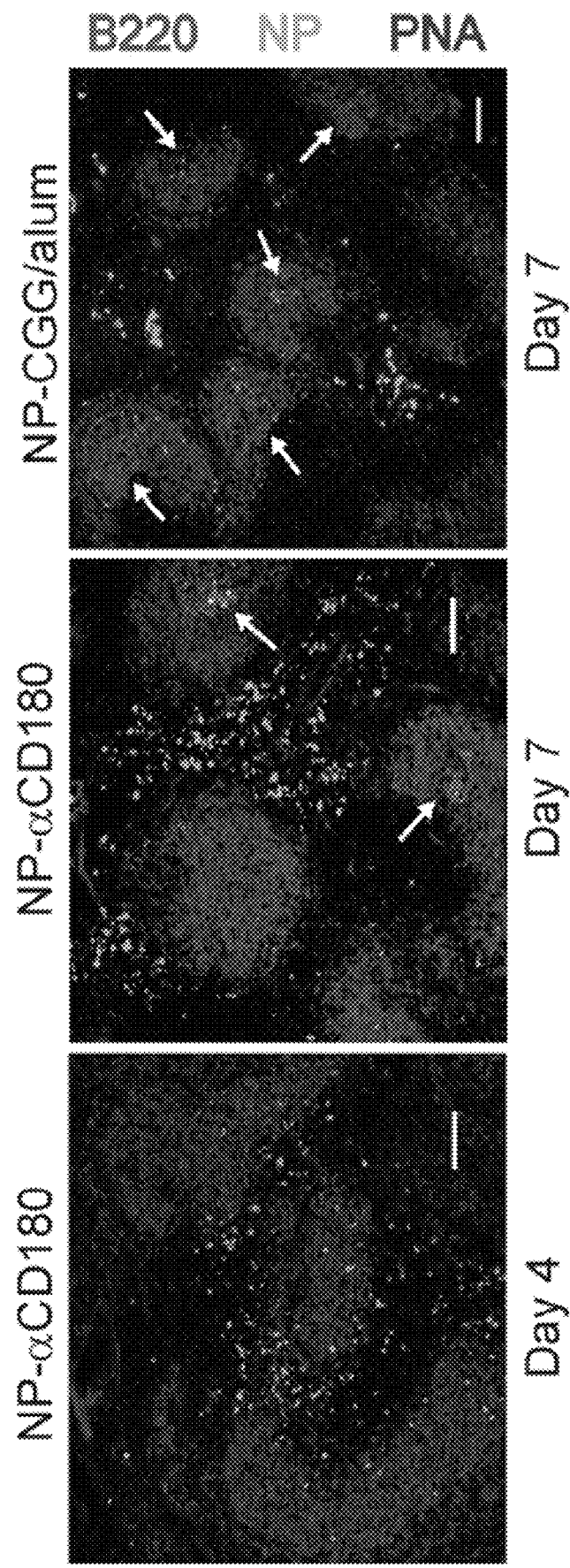
Figure 3H:
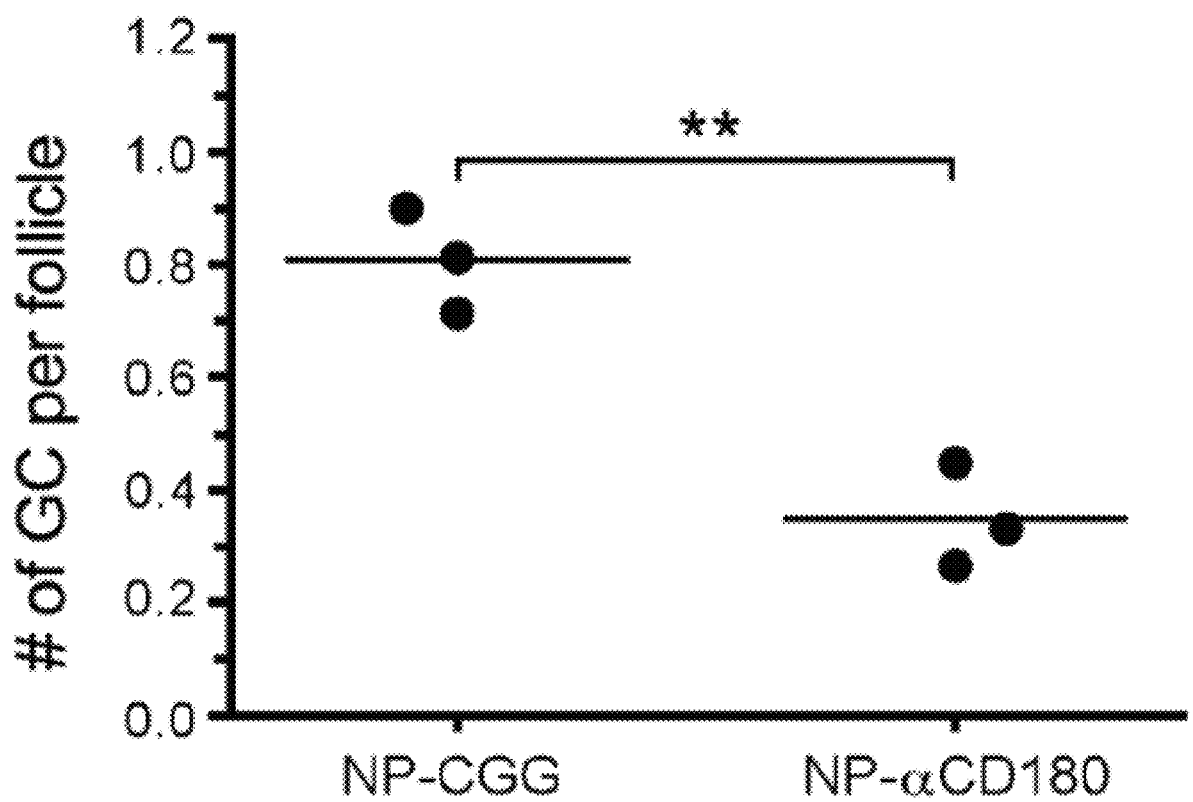
Figure 3I:
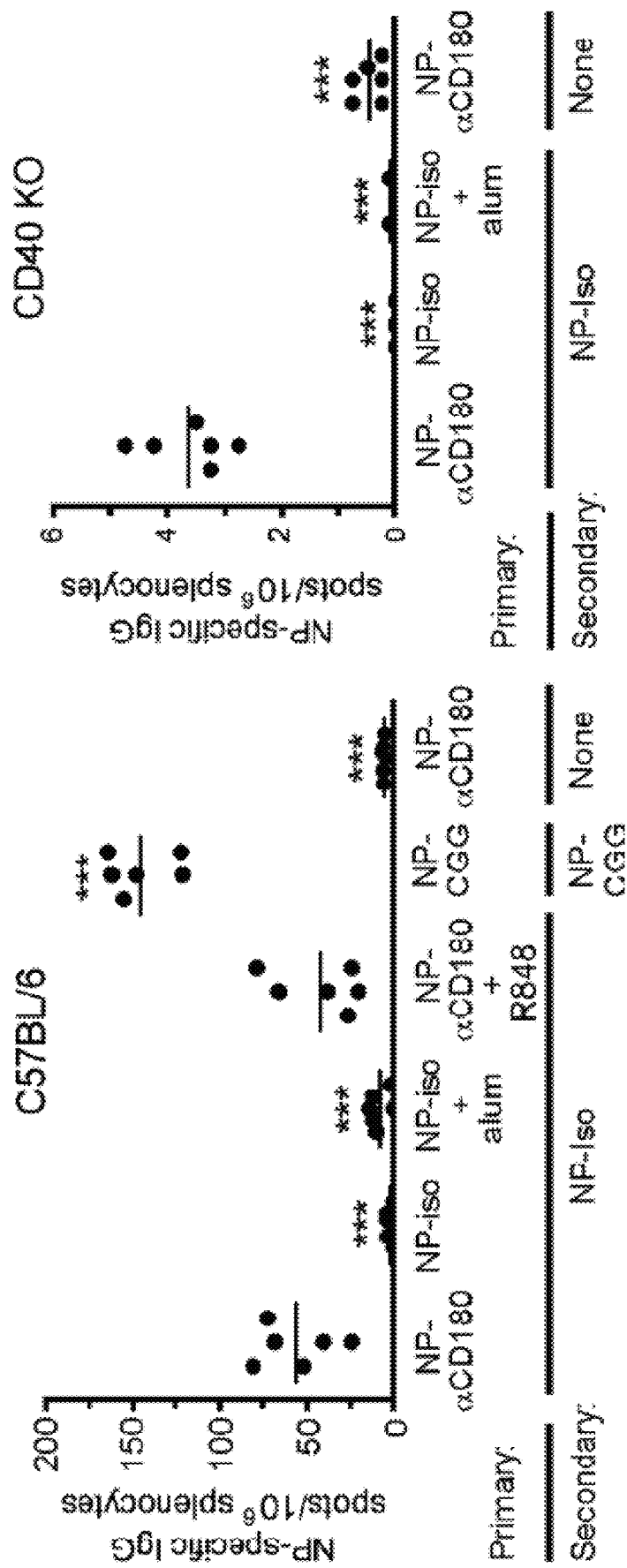

CD180 Targeting Induces Affinity Maturation, EF Responses, Germinal Center (GC) Formation and Immunologic Memory To assess whether CD180 targeting alone or with the addition of adjuvants could induce affinity maturation of Abs, we inoculated NP-αCD180 alone (50 µg i.v.) or co-administered with TLR-based adjuvants including CpG A or CpG B (TLR9), R848 (TLR7) or LPS (TLR4) and obtained sera 5, 7, or 28 d thereafter. To measure changes in relative affinity, we measured the relative binding of antisera to BSA with low levels of NP bound (NP2) vs. to BSA with higher levels of NP bound (NP20). For a negative control we immunized mice with NP-αDCIR2, which we had previously shown does not induce affinity maturation (Chappell et al., 2012). Following immunization with NP-αCD180, Ab affinity increased from days 5-7 (FIG. 3A) to levels significantly above the affinity after immunization with NP-αDCIR2, and this difference was still evident on d 28 (FIG. 3 B, bottom). Immunization of mice with unconjugated αCD180 plus TLR agonists had no effect on anti-NP Ab levels (data not shown). The addition of adjuvants along with NP-αCD180 did not change Ab affinity at d 7 (FIG. 3 B, top) even though it increased NP-specific IgM and IgG production 4- to 7-fold (FIG. 3 C). By d 28 after immunization the addition of a CpG adjuvant significantly increased affinity while the other adjuvants did not (FIG. 3 B, bottom). Unlike in WT mice, the affinity of the IgG Abs induced in CD40 KO mice did not increase above the levels of the negative controls (FIG. 3A).

To follow expansion and differentiation of Ag-specific B cells after immunization with NP-αCD180, we adoptively transferred splenocytes containing NP-specific B cells from Ly5.1+ B1-8hi mice (Shih et al., 2002) into Ly5.2+WT hosts. Spleens were harvested at d 4 or d 7 following inoculation with NP-αCD180 or NP-isotype control and analyzed by flow cytometry using sequential gating for B220+, Ly5.1+, and NP-APC binding. NP-isotype-treated mice showed no expansion of Ag-specific B220hi B cells, while NP-αCD180-treated mice showed an approximately 20-fold expansion at both time points (FIG. 3 D). This expansion included GL7+PNA+GC B cells, which increased in number by d 7 (FIG. 3 E). By d 7 the NP-αCD180-treated mice also had significant numbers of CD138+ antibody forming cells (AFCs) in the spleen (FIG. 3 F). These results suggested that NP-αCD180 induces both EF Ab responses and GC formation. Indeed, by d 4 the spleens of NP-αCD180-treated mice had large numbers of Ag-specific B cells in EF sites and by d 7 PNA+ GCs were evident (FIG. 3 G). By comparison, GCs induced by NP-αCD180 were generally smaller (FIG. 3 G) and present in fewer numbers (FIG. 3 H) than those induced by NP-CGG plus alum.

The presence of GCs in NP-αCD180-treated mice suggested that the Ag-specific B cell expansion induced by Ag-αCD180 leads to the development of immunologic memory, which is characterized by the ability to rapidly generate Ag-specific AFCs in response to soluble Ag re-challenge. To test this, we immunized groups of WT and CD40 KO mice with NP-conjugated mAbs as above or with NP-chicken gamma globulin (CGG) in alum as a positive control. After 10 weeks mice were boosted with matched soluble Ag (NP-isotype or NP-CGG) or with PBS as a negative control. On d 4 post-boost spleens were harvested and the number of IgG-producing AFCs was assessed using an NP-specific IgG ELISPOT™ assay. As expected, WT mice primed with NP-CGG in alum produced significant numbers of IgG-producing AFCs when boosted with soluble Ag (FIG. 3 I, left). In contrast to mice primed with NP-isotype, NP-αCD180-primed mice contained low but detectable numbers of Ag-specific long-lived plasma cells (LLPCs) in the spleen 10 weeks following immunization (0.0 vs. 5.7+/−0.8 SEM per $10^6$ splenocytes). Levels of Ag-specific AFCs increased approximately 10-fold upon re-challenge with soluble Ag (56+/−8.7 SEM per $10^6$ splenocytes). The number of AFCs generated in mice primed with NP-αCD180 in the absence of adjuvant was roughly one third that of NP-CGG in alum primed mice. This result is in accord with smaller GC induction by NP-αCD180 compared to NP-CGG plus alum (FIGS. 3 G and 3 H). However, the spot size was three times as large as spots from mice primed with NP-CGG (data not shown), suggesting that the amount of NP-specific IgG produced per AFC was greater. Addition of the adjuvant R848 during the primary immunization with NP-αCD180 neither increased the spot number nor spot size upon Ag re-challenge compared to mice primed with NP-αCD180 alone.

Surprisingly, following re-challenge with soluble Ag, we also detected some NP-specific IgG-secreting AFCs in CD40 KO mice primed with NP-αCD180 (FIG. 3 I, right). While the number of NP-specific IgG-secreting AFCs in CD40 KO mice was roughly ¹⁄₁₅th the number in WT mice, this number was significantly higher than in PBS-boosted CD40 KO mice or CD40 KO mice primed with Ag in alum. Thus, CD180 targeting effectively primes for immunologic memory in WT mice, and to a lesser extent even in the absence of CD40.

Ag-Specific B Cells are Efficiently Activated by Linking BCR and CD180 Stimuli

The fact that specific Ag must be linked to anti-CD180 in order to induce IgG Ab responses (FIG. 2 C) suggested that both BCR and CD180 ligation on the same cell are required for specific Ab to be produced. To test this possibility, first we compared the activation of B cells following stimulation in vivo through either the BCR, CD180, or through both receptors. We used B1-8hi mice that contain NP-specific B cells (Shih et al., 2002); groups of these mice were injected with either 100 μg NP-αCD180 or with NP-isotype and spleens harvested 24 hrs later. The NP-specific B cells (6-10%) were distinguished from total CD19+ B cells by staining with NP-APC. Four groups of CD19+ B cells were then analyzed ex vivo for their expression of CD69, CD86, MHC class II, and the receptor, transmembrane activator and calcium-modulator and cyclophilin ligand interactor (TACI): unstimulated B cells (NP− B cells from NP-isotype-treated mice), BCR-stimulated B cells (NP+ B cells from NP-isotype treated mice), CD180-stimulated B cells (NP− B cells from NP-αCD180 treated mice), and B cells stimulated through both the BCR and CD180 stimulated (NP+ B cells from NP-αCD180 treated mice). Compared to unstimulated B cells, B cells stimulated via either Ag or αCD180 had increased expression of CD86 and TACI (FIG. 4A). However, over a series of experiments, the levels of CD69, CD86, and TACI were significantly higher on B cells stimulated through both the BCR and CD180 at 24 h (FIGS. 4A and B) and later time points (data not shown). Thus, the combination of BCR and CD180 signaling in vivo appears to be more effective at activating B cells than either signal alone.

B Cell Expression of CD180 is Necessary and Sufficient for Ag-αCD180 Driven Ab Responses The data in FIG. 4 suggest that the powerful adjuvant effect of Ag-αCD180 may be mediated by the combination of BCR and CD180 signaling of B cells. However, since CD180 is expressed on both B cells and non-B cells, Ab responses induced by CD180 targeting may be mediated by either delivery of both Ag-mediated BCR signaling together with CD180 signals to Ag-specific B cells and/or CD180 delivery and signaling to non-B cells which then in turn stimulate Ag-specific B cell and T cell responses. To distinguish these possibilities we carried out adoptive transfers to establish mice that express CD180 only on B cells, only on non-B cells, or on both B cells and non-B cells (FIG. 5A). B cell deficient μMT mice were inoculated with CD180 KO B cells to create mice where CD180 was expressed only on non-B cells. These mice failed to make Ag-specific IgG after inoculation with NP-αCD180 (FIG. 5 B), demonstrating that CD180 expression on B cells is necessary to generate an Ab response after CD180 targeting. CD180 KO recipients, into which purified CD180+ B cells were transferred, expressed CD180 only on B cells and not on non-B cells. Following immunization with NP-αCD180, these mice produced high levels of Ag-specific IgG. These data show that CD180 expression on B cells is sufficient for CD180-based targeting. B cell deficient (μMT) mice into which CD180+ B cells were transferred so that CD180 was expressed on both B cells and non-B cells made somewhat more NP-specific IgG than mice not expressing CD180 on non-B cells (FIG. 5 B). This suggests that CD180 expression on non-B cells such as DCs, while neither sufficient nor essential for Ag targeting, influences the extent of IgG production.

When anti-CD180 mAb is inoculated i.v. into mice, it binds to CD180+CD19+ B cells and to other CD180+ cells in the spleen including CD11c+ DCs and F4/80+ macrophages, but not to CD3+ T cells, which do not express CD180 (data not shown). To determine which APCs were most effective at priming T cells following targeting to CD180, WT mice were inoculated with either OVA-isotype or OVA-αCD180; 16 h later B cells and DCs were purified by negative selection and co-cultured with CFSE-labeled OVA-specific OT-II CD4 T cells or OT-I CD8 T cells. After 72 h the levels of CFSE in the OVA-specific T cells were measured by flow cytometry (FIG. 5 C). OVA-αCD180 targeted B cells, unlike B cells from OVA-isotype treated control mice, clearly induced proliferation of Ag-specific CD4 T cells. However, OVA-αCD180-targeted DCs were much more effective on a per cell basis at stimulating OT-II proliferation. OVA-αCD180 targeted B cells, unlike OVA-αCD180 targeted DCs, failed to induce any proliferation of OVA-specific OT-I CD8 T cells, consistent with the poor cross-presentation of Ag by B cells compared to DCs. Thus, while DCs are not required for the Ag-specific Ab responses induced by Ag-αCD180, they may function to stimulate Ag-specific CD4 helper T cells required for optimal IgG production.

IL4, IFN-α/β Signaling and Mature B Cells are not Required for Ag-Targeting to CD180

Type I interferon (IFN) has been shown to act directly on B cells and promote Ab responses (LeBon et al., 2005, Fink et al., 2006) Thus, we compared IgG responses of type 1 IFN α/β receptor (IFNα/βR) KO and WT mice after inoculating NP-αCD180; abrogating signaling through the IFNα/βR if anything increased anti-NP IgG production, suggesting that type 1 IFNs may normally restrain Ab responses induced via CD180. Mice deficient in MHC class II (MHC II KO) after immunization with NP-αCD180 had a more severe reduction in anti-NP IgG production than either CD40 or TCR KO mice (FIG. 6A). The reason for this is not clear as B cell levels are normal in MHC II KO mice, and MHC II B cells respond normally to TI Ags (Markowitz et al., 1993). Another T cell-dependent B cell activator, αIgD, requires the action of IL-4 (Finkelman et al., 1986), so we compared Ab responses of WT, IL4 KO and OX40L KO mice inoculated with NP-αCD180. After CD180 targeting both IL-4 KO and OX40L KO mice produced anti-NP IgG at levels similar to WT controls (FIG. 6 A, B), demonstrating that the IL-4-Th2 pathway is not required during CD180 targeting.

In order to assess a possible role for the cytokine BAFF in CD180 targeting, we immunized BAFF-R KO mice, which have a near complete block in mature B cell development (Sasaki et al., 2004). To our surprise BAFF-R KO mice produced normal levels of NP-specific IgG Abs following targeting to CD180 (FIG. 6A). This suggests that while CD180+ B cells are required for Ag-αCD180 targeting, mature B cells may not be necessary. Indeed, we observed significant increases in both FO (B220+CD23hi CD21int) and T1/T2 (B220+CD23lo CD21lo CD93+) transitional B cells on days 1 and 3 following immunization with NP-αCD180 compared to NPisotype-injected animals (FIG. 6 C). In contrast, B cells with a MZ phenotype (B220+ CD23lo CD21hi CD93−) showed a marked decrease following NP-αCD180 administration. These results demonstrate that NP-αCD180 expands some but not all splenic B cell subsets. Since BAFF can bind to TACI and BCMA as well as BAFF-R (Rickert et al., 2011), it remains possible that signaling through TACI or BCMA contributes to Ag-αCD180-driven IgG responses.

Discussion

Collectively, our data indicate that targeting Ags to CD180 induces rapid activation of Ag-specific B cells, leading to significant IgG production within 7 days. Remarkably, a single injection of Ag-αCD180 without any additional adjuvant also led to the development of both Ab affinity maturation and immunologic memory (FIG. 3). Furthermore, while severely impaired, Ag-specific IgG production and responses to secondary immunizations were retained in CD40 KO mice (FIG. 3 H), even though CD40 KO mice did not make Ag-specific IgG or develop memory Ab producing cells in response to Ag in alum, as reported previously (Kawabe et al., 1994). The Ab responses induced required the Ags to be attached to anti-CD180 and could be induced to both haptens and protein Ags.

Why is this mode of immunization so effective in rapidly raising IgG Ab responses? Several lines of evidence suggest that it is the combination of simultaneous signaling of Ag-αCD180 through both the BCR and CD180 on B cells that promotes the rapid Ab responses. First, effective induction of IgG by Ag-αCD180 required CD180 to be expressed on B cells and not on other cells. Second, while Ab responses to linked Ag occurred with both NP-αCD180 and OVA-αCD180, there was little or no response to soluble Ags co-administered at the same time. Third, B cells activated in vivo by stimulating the Ag receptor and CD180 together expressed higher levels of activation markers than B cells triggered by either stimulus alone (FIG. 4). Indeed, the greater induction of CD86 expression after co-ligation of the BCR and CD180 may well be a feature of targeting Ag to CD180, as CD86 is necessary for IgG responses to non-adjuvanted Ag (Borriello et al., 1997). The TACI receptor was also induced to higher levels after CD180 targeting, and TACI plays a role in class switching and IgG production (He et al., 2010).

Ag targeting to CD180, while requiring B cells, does not appear to require mature B cells: BAFF-R KO mice mainly have transitional 1 (T1) B cells; they have a fivefold reduction in transitional 2 B cells and are almost completely deficient of mature follicular and marginal zone B cells (Sasaki et al., 2004). Nevertheless, inoculation of Ag-αCD180 into BAFF-R KO mice produced as much Ag-specific IgG as in WT mice. This suggests that T1 B cells are a major target for Ag-anti-CD180. Although T1 B cells readily apoptose following BCR stimulation alone, they do not die when signaled via BCR and a second signal (Kovesdi et al., 2004), T1 B cells also constitutively express activation-induced deaminase (AID) (Ucda et al, 2007, Han et al., 2007, Kuraoka et al., 2009) and can rapidly produce large quantities of IgG and undergo somatic mutation when triggered with a combination of BCR and TLR stimuli (Mao et al., 2004, Ueda et al., 2007, Han et al., 2007, Capolunghi et al., 2008, Aranburu et al., 2010, Kuraoka et al., 2011). Thus, AID+T1 B cells signaled through both the BCR and CD180 may rapidly switch and mature into IgG-producing plasma cells.

Our results indicate that Ag-αCD180 targeting generates long-lived plasma cells and switched memory B cells in both WT and CD40 KO mice. First, the t1/2 of Ag-specific IgG in immunized WT mice was approximately 38 days (based on the kinetics in FIG. 2A), while catabolism of a discrete burst of IgG from a short-lived AFC response would have a t1/2 of 21 days. Additionally, Ag-specific IgG levels in CD40 KO mice continue to rise over time. Both of these results require continual IgG production to slow or offset the constant elimination IgG, implying that some Ab-producing cells are retained. Second, Ag-specific GL7+PNA+GC B cells were evident by d 7 after immunization with NP-αCD180. This GC phenotype suggests memory B cell precursors were being generated. Third, both WT and CD40 KO mice had significantly more AFCs following Ag boost than mice primed with Ag-isotype or mice not boosted (FIG. 3 I). Many studies have implicated CD40 signals in the induction of memory B cells by TD or TI-2 Ag (Taylor et al., 2012, Kaji et al., 2012), and indeed a much stronger memory response was induced by NP-αCD180 in WT mice than in CD40 KO mice. However, NP-αCD180 clearly induced some CD40-independent B cell memory. TI Ags can induce T cell-independent GC-independent memory B cell responses (Zhang et al., 1988, Weller et al., 2001, Defrance et al., 2011, Berkowska et al., 2012). Thus, in addition to the generation of strong EF responses, stimulation through CD180, when combined with BCR signaling, may be a novel pathway of T-independent memory B cell differentiation.

Although CD40 KO and TCR-deficient mice still can make IgG after CD180 targeting, the amount of Ag-specific IgG is only about 10% of that in WT mice. Thus, T cells clearly are required for most of the IgG response. Since CD180 is expressed on both B cells and DCs and internalizes following ligation by mAb (data not shown), it was likely that CD180 targeting could deliver Ag both to Ag-specific B cells as well as to DCs that don't bind Ag. Indeed, this was the case: DCs targeted in vivo via αCD180 were more efficient than targeted B cells in stimulating CD4 T cell proliferation. Although Ab responses induced by αCD180 only required CD180 expression on B cells, it appears that DC-mediated T cell priming helped promote a greater response to CD180 targeting in WT mice than if Ag were solely directed to B cells (FIG. 5 B).

The combined Ag targeting/adjuvant method described here can be used for human vaccines. Most vaccines do not induce protective immunity in all individuals, and most vaccines do not induce lasting immunity. Furthermore, vaccination of immuno-compromised individuals requires special considerations and approaches (Rappuoli et al., 2011, Miller and Rathore, 2012). Targeting to CD180 induces IgG responses and some immunologic memory even in CD40 KO mice, and, remarkably, induces high levels of IgG Abs even in mature B cell-deficient BAFF-R KO mice and IFN-signaling-deficient IFNα/βR KO mice. Thus, a CD180-based vaccine platform can be used for immunizing immuno-compromised people including the elderly. In addition, most vaccine strategies require more than one injection in order to produce sufficient circulating levels of protective Abs. Single dose vaccines provide a number of advantages (Bowick and McAuley, 2011, Levine, 2011) and one injection of Ag attached to anti-CD180 induces a rapid and strong IgG response. Thus, a single inoculation of a CD180-based vaccine can produce protective humoral immunity and be a particularly attractive approach for therapeutic vaccination shortly after an exposure to a pathogen.

Materials and Methods

Mice

C57BL/6, CD40 KO, OT-I OVA-specific CD8+ TCR transgenic, OT-II OVA-specific CD4+ TCR transgenic, B cell-deficient (µMT), and T cell-deficient (TCRβ/δ KO) mice were purchased from Jackson Laboratory (Bar Harbor, ME). All strains were on the C57BL/6 background unless otherwise noted. CD180 KO, MHC II KO, and IFNα/βR KO mice were gifts from S. Skerrett, P. Fink and K. Murali-Krishna, respectively (University of Washington, Seattle, WA). OX40L KO mice were a gift from A. H. Sharpe (Harvard University, Cambridge, MA). BAFF-R KO mice were a gift from K. Rajewsky (Harvard Medical School, Boston, MA). B6.SJL-B1-8hi knockin Ly5.1 mice were a gift from M. Nussenzweig (Rockefeller University, New York, NY). IL-4 KO mice on the BALB/c background were a gift from S. Ziegler (Benaroya Research Institute, Seattle, WA), and WT control BALB/c mice were purchased from the Jackson Laboratory. All mice were sex- and age-matched and used at six to ten weeks of age. The University of Washington Institutional Animal Care and Use Committee approved all animal work.

Cell Preparation and Adoptive Transfers

Total splenocytes were processed by mechanical disruption and erythrocytes were depleted by Gey's lysis. For adoptive transfer experiments in FIG. 3, splenocytes from B1-8hi IgH transgenic mice were labeled with PE-conjugated NP and anti-B220-FITC to determine the frequency of Ag-specific B cells by flow cytometry. Total splenocytes containing $2 \times 10^5$ NP-binding B cells were transferred i.v. to individual B6 recipients 24 h prior to immunization. For experiments in FIGS. 5A and B, splenic B cells from WT or CD180-deficient mice were isolated by three rounds of negative selection enrichment (STEMCELL Technologies, Vancouver, BC, Canada). $10 \times 10^6$ purified B cells of appropriate genotype were transferred i.v. to recipients as indicated 24 h prior to immunization. For experiments in FIG. 5C, CD4 and CD8 T cells from OTII and OT-I TCR transgenic mice, respectively, and DCs or B cells from immunized C57BL/6 mice were isolated by three rounds of negative selection enrichment using the appropriate kit (STEMCELL Technologies, Vancouver, BC, Canada). Purities for all cell enrichments were >99% as determined by flow cytometry for CD19 (B cells), CD4 or CD8 (T cells), or CD11c (DCs). Frequencies of OT-I and OT-II T cells were determined within the CD3+ T cell population by staining for Vα2 and used to determine final numbers for cell culture.

In Vitro CFSE Proliferation Assay $5 \times 10^4$ B cells or DCs from immunized mice were enriched as described above and co-cultured with titrating numbers of CFSE-labeled Vα2+OT-I or OT-II T cells in 96-well round bottom plates for 3 days at 37 C, 5% CO2 as previously described (Chaplin et al., 2011). CFSE (Invitrogen) labeling was performed as previously described (Chaplin et al., 2011).

ELISA and ELISPOT Assays

For ELISA assays, polystyrene plates were coated with either 2 µg/mL anti-mouse IgG (H+L) (Jackson ImmunoResearch, West Grove, PA) for total Ig, 20 µg/mL NiP-BSA (Biosearch Technologies, Novato, CA) for NP-specific Ab, or 20 µg/mL OVA (Sigma-Aldrich). Affinity determinations were performed as described previously (Herzenberg et al., 1980, Chappell et al., 2012), using custom NiP2- and NiP20-BSA prepared by conjugation to the succinimidyl ester of NiP (Biosearch Technologies) according to manufacturer instructions. Detection and analyses were performed as previously described (Chaplin et al., 2011). ELISPOT assays were performed as previously described (Goins et al., 2010). Spot number and size were quantified using a CTL-ImmunoSpot™ S5 Core Analyzer ELISPOT™ reader with ImmunoSpot™ Academic V5.0 software (Cellular Technology Ltd., Shaker Heights, OH).

Flow Cytometry

Flow cytometry analyses were performed on a FACSCanto™ (Becton Dickinson, Franklin Lakes, NJ). A minimum of 30,000 cells of the final gated population was used for all analyses. Data analyses were performed with FlowJo™ (Tree Star, Ashland, OR) software. Stainings were performed for: CD3, CD80, and CD95 (Becton Dickinson mAbs 145-2C11, 16-10A1, and Jo2, respectively); CD4, CD8a, TCR Vα2, CD19, CD86, CD11b, CD11c, F4/80, and CD69 (BioLegend, San Diego, CA, mAbs RM4-5, 53-6.7, B20.1, 6D5, GL-1, M1/70, N418, BM8, and H1.2F3, respectively); B220, GL7, Ly5.1 (eBioscience, San Diego, CA, mAbs RA3-6B2, GL-7, and A20, respectively); FITC labeled peanut agglutinin (FITC-PNA) was obtained from Vector Labs (Burlingame, CA); anti-MHC II (NIMR-4) from Southern Biotech (Birmingham, AL); and anti-TACI/TNFSF13b (mAb 166010) from R&D Systems (Minneapolis, MN). NP-APC and NPPE were prepared by conjugation of NP-Osu (Biosearch Technologies, Novato, CA) to allophycocyanin or phycoerythrin (both from Sigma-Aldrich) as described for NP2-BSA above. All isotype control mAbs were purchased from BioLegend.

Other Antibodies and Reagents

The anti-CD180 (RP/14) hybridoma was a kind gift from K. Miyake (University of Tokyo, Tokyo, Japan) and the rat IgG2a isotype control (9D6) hybridoma was a gift from R. Mittler (Emory University, Atlanta, GA). To ensure equivalence these mAb were sequentially purified on the same protein G column and tested for endotoxin by LAL gel-clot assays in GlucaShield™ buffer (Associates of Cape Cod, East Falmouth, MA). Samples were rejected if endotoxin levels were above 0.025 EU/mg protein. mAbs were conjugated to NP as described for NP2-BSA above. Final NP-mAb conjugation ratios ranged from NP6 to NP19 as determined by spectrophotometry. In all inoculations the NP ratios were always higher for the paired isotype than anti-CD180 to control for any possible effects due to TI-2 Ag signaling. Chicken OVA (Sigma-Aldrich) was conjugated to mAbs as previously described (Weir et al., 1986) with an average conjugation ratio of 2 OVA per mAb as determined by electrophoresis. Amount of conjugate administered refers to the mAb component, i.e., 100 µg OVA-αCD180 contains a total mass of 156 µg OVA-αCD180 due to addition of 56 µg OVA to 100 µg of αCD180. Mice were inoculated i.v. with a fixed volume of 200 µl in PBS except for immunizations with Ag in alum, which were administered i.p. Alum-precipitated antigens were prepared with Imject™ (Thermo Fisher Scientific) according to the manufacturer's instructions. LPS (L2143) was from Sigma-Aldrich. Synthetic TLR agonists R848, and CpG ODN1585 (type A)/ODN1826 (type B) were from InvivoGen (San Diego, CA). When used, agonists were admixed with the immunogen and administered in the 200 µL i.v. bolus.

Immunohistochemistry

8 µM frozen spleen sections obtained from mice immunized 4 or 7 days previously with 100 µg NP-αCD180, NP-isotype, or NP-CGG plus alum were stained with anti-B220-eFluor450 (eBioscience), PNA-FITC (Vector Labs) and NP-PE as previously described (Chappell et al., 2012). Images were collected on an LSM 510 META™ confocal microscope (Carl Zeiss) with LSM 510 (v 4.2) software (Carl Zeiss) using 10× objectives at room temperature. Images were processed using ImageJ™ (National Institutes of Health) and Photoshop™ (Adobe) software.

Statistical Analyses

Raw data of experimental groups were analyzed either by one-way ANOVA followed by Bonferroni's Multiple Comparison Test (GraphPadPrism™ software, version 4.0a for Macintosh, San Diego, CA) or by two-tailed, type two Student's t-test for individual paired columns. Columnar data are represented as mean+/−standard error (SEM). A value of p<0.05 was considered to be statistically significant and assigned *, while p<0.01 and p<0.001 were assigned  and *, respectively.

REFERENCES FOR EXAMPLE 1

Alving, C. R., K. K. Peachman, M. Rao and S. G. Reed 2012. Adjuvants for human vaccines. *Curr. Opin. Immunol.* 24:310-315.

Aranburu, A., C. Ceccarelli, E. Giorda, R. Lasorella, G. Ballatore, and R. Carsetti. 2010. TLR ligation triggers somatic hypermutation in transitional B cells inducing the generation of IgM memory B cells. *J. Immunol.* 185: 7293-301.

Berkowska, M. A., G. J. Driessen, V. Bikos, C. Grosserichter-Wagener, K. Stamatopoulos, A. Cerutti, B. He, K. Biermann, J. F. Lange, M. van der Burg, J. J. van Dongen, and M. C. van Zelm. Human memory B cells originate from three distinct germinal center-dependent and -independent maturation pathways. *Blood.* 118:2150-2158.

Borriello, F., M. P. Sethna, S. D. Boyd, A. N. Schweitzer, E. A. Tivol, D. Jacoby, T. B. Strom, E. M. Simpson, G. J. Freeman, and A. H. Sharpe. 1997. B7-1 and B7-2 have overlapping, critical roles in immunoglobulin class switching and germinal center formation. *Immunity.* 6:303-313.

Bowick, G. C., and A. J. McAuley. 2011. Vaccine and adjuvant design for emerging viruses: mutations, deletions, segments and signaling. *Bioeng. Bugs.* 2:129-35.

Caminschi, I., and K. Shortman 2012. Boosting antibody responses by targeting antigens to dendritic cells. *Trends Immunol.* 33:71-77.

Caminschi, I., M. H. Lahoud, and K. Shortman K. 2009. Enhancing immune responses by targeting antigen to DC. *Europ. J. Immunol.* 39:931-938.

Capolunghi, F., S. Cascioli, E. Giorda, M. M. Rosado, A. Plebani, C. Auriti, G. Seganti, R. Zuntini, S. Ferrari, M. Cagliuso, I. Quinti, and R. Carsetti. 2008. CpG drives human transitional B cells to terminal differentiation and production of natural antibodies. *J. Immunol.* 180:800-8.

Carter, R. W., C. Thompson, D. M. Reid, S. Y. Wong, and D. F. Tough. 2006. Preferential induction of CD4+ T cell responses through in vivo targeting of antigen to dendritic cell-associated C-type lectin-1. *J. Immunol.* 177:2276-2284.

Chan, V. W., I. Mecklenbrauker, I. Su, G. Texido, M. Leitges, R. Carsetti, C. A. Lowell, K. Rajewsky, K. Miyake, and A. Tarakhovsky. 1998. The molecular mechanism of B cell activation by Toll-like receptor protein RP-105. *J. Exp. Med.* 188:93-101.

Chaplin, J. W., S. Kasahara, E. A. Clark, and J. A. Ledbetter. 2011. Anti-CD180 (RP105) activates B cells to rapidly produce polyclonal Ig via a T cell and MyD88-independent pathway. *J. Immunol.* 187:4199-209.

Chappell, C. P., K. E. Draves, N. V. Giltiay, and E. A. Clark. 2012. Extrafollicular B cell activation by marginal zone dendritic cells drives T cell-dependent antibody responses. *J. Exp. Med.* 209:1825-1840.

Clark, E. A., and G. Shu. 1990. Association between IL-6 and CD40 signaling. IL-6 induces phosphorylation of CD40 receptors. *J. Immunol.* 145:1400-6.

Clark, E. A., G. L. Shu, B. Lüscher, K. E. Draves, J. Banchereau, J. A. Ledbetter, and M. A. Valentine. 1989. Activation of human B cells. Comparison of the signal transduced by IL-4 to four different competence signals. *J. Immunol.* 143:3873-80.

Defrance, T., M. Taillardet, and L. Genestier. 2011. T cell-independent B cell memory. *Curr. Opin. Immunol.* 23:330-6.

Denis, O., D. Latinne, F. Nisol, and H. Bazin. 1993. Resting B cells can act as antigen presenting cells in vivo and induce antibody responses. *Int. Immunol.* 5:71-8.

Dudziak, D., A. O. Kamphorst, G. F. Heidkamp, V. R. Buchholz, C. Trumpfheller, S. Yamazaki, C. Cheong, K. Liu, H. W. Lee, C. G. Park, R. M. Steinman, and M. C. Nussenzweig. 2007. Differential antigen processing by dendritic cell subsets in vivo. *Science.* 315:107-11.

Fink, K., K. S. Lang, N. Manjarrez-Orduno, T. Junt, B. M. Senn, M. Holdener, S. Akira, R. M. Zinkernagel, and H. Hengartner. 2006. Early type I interferon-mediated signals on B cells specifically enhance antiviral humoral responses. *Europ. J. Immunol.* 36:2094-2105.

Finkelman, F. D., J. Ohara, D. K. Goroff, J. Smith, N. Villacreses, J. J. Mond, and W. E. Paul. 1986. Production of BSF-1 during an in vivo, T-dependent immune response. *J. Immunol.* 137:2878-2885.

Goins, C. L., C. P. Chappell, R. Shashidharamurthy, P. Selvaraj, and J. Jacob. 2010. Immune complex-mediated enhancement of secondary antibody responses. *J. Immunol.* 184:6293-8.

Han, J. H., S. Akira, K. Calame, B. Beutler, E. Selsing E, and T. Imanishi-Kari. 2007. Class switch recombination and somatic hypermutation in early mouse B cells are mediated by B cell and Toll-like receptors. *Immunity.* 27:64-75.

He, B., R. Santamaria, W. Xu, M. Cols, K. Chen, I. Puga, M. Shan, H. Xiong, J. B. Bussel, A. Chiu, A. Puel, J. Reichenbach, L. Marodi, R. Doffinger, J. Vasconcelos, A. Issekutz, J. Krause, G. Davies, X. Li, B. Grimbacher, A. Plebani, E. Meffre, C. Picard, C. Cunningham-Rundles, J. L. Casanova, and A. Cerutti. 2010. The transmembrane activator TACI triggers immunoglobulin class switching by activating B cells through the adaptor MyD88. *Nat. Immunol.* 11:836-845.

Hebeis, B. J., E. Vigorito, and M. Turner. 2004. The p110delta subunit of phosphoinositide 3-kinase is required for the lipopolysaccharide response of mouse B cells. *Biochem. Soc. Trans.* 32:789-791.

Hebeis, B. J., E. Vigorito, D. Kovesdi, and M. Turner. 2005. Vav proteins are required for B-lymphocyte responses to LPS. *Blood.* 106:635-640.

Herzenberg, L. A., S. J. Black, T. Tokuhisa, and L. A. Herzenberg. 1980. Memory B cells at successive stages of differentiation. Affinity maturation and the role of IgD receptors. *J. Exp. Med.* 151:1071-1087.

Kaji, T., A. Ishige, M. Hikida, J. Taka, A. Hijikata, M. Kubo, T. Nagashima, Y. Takahashi, T. Kurosaki, M. Okada, O. Ohara, K. Rajewsky, and T. Takamori. 2012. Distinct cellular pathways select germline-encoded and somatically mutated antibodies into immunological memory. *J. Exp. Med.* 209:2079-97.

Kawabe, T., T. Naka, K. Yoshida, T. Tanaka, H. Fujiwara, S. Suematsu, N. Yoshida, T. Kishimoto, and H. Kikutani. 1994. The immune responses in CD40-deficient mice:

impaired immunoglobulin class switching and germinal center formation. *Immunity.* 1:167-178.

Kawamura, H., and J. A. Berzofsky. 1986. Enhancement of antigenic potency in vitro and immunogenicity in vivo by coupling the antigen to anti-immunoglobulin. *J. Immunol.* 136:58-65.

Kovesdi, D., K. Paszty, A. Enyedi, E. Kiss, J. Matko, K. Ludanyi, E. Rajnavolgyi, and G. Sarmay. 2004. Antigen receptor-mediated signaling pathways in transitional immature B cells. *Cell Signal.* 16:881-9.

Kuraoka, M., D. Liao, K. Yang, S. D. Allgood, M. C. Levesque, G. Kelsoe, and Y. Ueda. 2009. Activation-induced cytidine deaminase expression and activity in the absence of germinal centers: insights into hyper-IgM syndrome. *J. Immunol.* 183:3237-48.

Kuraoka, M., L. McWilliams, and G. Kelsoe. 2011. AID expression during B-cell development: searching for answers. *Immunol. Res.* 49:3-13.

Lahoud, M. H., F. Ahmet, S. Kitsoulis, S. S. Wan, D. Vremec, C. N. Lee, B. Phipson, W. Shi, G. K. Smyth, A. M. Lew, Y. Kato, S. N. Mueller, G. M. Davey, W. R. Heath, K. Shortman, and I.

Caminschi. 2011. Targeting antigen to mouse dendritic cells via Clec9A induces potent CD4 T cell responses biased toward a follicular helper phenotype. *J. Immunol.* 187: 842-50.

Le Bon, A., C. Thompson, E. Kamphuis, V. Durand, C. Rossmann, U. Kalinke, and D. F. Tough. 2006. Cutting edge: enhancement of antibody responses through direct stimulation of B and T cells by type I IFN. *J. Immunol.* 176:2074-2078.

Levine MM. 2011. "IDEAL" vaccines for resource poor settings. *Vaccine.* 29 Suppl 4:D116-25. Mao, C., L. Jiang, M. *Melo*-Jorge, M. Puthenveetil, X. Zhang, M. C. Carrol, and T. Imanishi-Kari. 2004. T cell-independent somatic hypermutation in murine B cells with an immature phenotype. *Immunity.* 20:133-44.

Markowitz, J. S., P. R. Rogers, M. J. Grusby, D. C. Parker, and L. H. Glimcher. 1993. B lymphocyte development and activation independent of MHC class II expression. *J. Immunol.* 150:1223-33.

Miller, M. A., and M. H. Rathore. 2012. Immunization in special populations. *Adv. Pediatr.* 59:95-136.

Miyake, K., Y. Yamashita, Y. Hitoshi, K. Takatsu, and M. Kimoto. 1994. Murine B cell proliferation and protection from apoptosis with an antibody against a 105-kD molecule: unresponsiveness of X-linked immunodeficient B cells. *J. Exp. Med.* 180:1217-1224.

Miyake, K., Y. Yamashita, M. Ogata, T. Sudo, and M. Kimoto. 1995. RP105, a novel B cell surface molecule implicated in B cell activation, is a member of the leucine-rich repeat protein family. *J. Immunol.* 154:3333-3340.

Nagai, Y., T. Kobayashi, Y. Motoi, Y. Ishiguro, S. Akashi, S. Saitoh, Y. Kusumoto, T. Kaisho, S. Akira, M. Matsumoto, K. Takatsu, and K. Miyake. 2005. The radioprotective 105/MD-1 complex links TLR2 and TLR4/MD-2 in antibody response to microbial membranes. *J Immunol.* 174:7043-9.

Rappuoli, R., C. W. Mandl, S. Black, and E. De Gregorio. 2011. Vaccines for the twenty-first century society. *Nat. Rev. Immunol.* 11:865-72.

Rickert, R. C., J. Jellusova, and A. V. Miletic. 2011. Signaling by the tumor necrosis factor receptor superfamily in B-cell biology and disease. *Immunol. Rev.* 244:115-33.

Sancho, D., and C. Reis e Sousa. 2012. Signaling by myeloid C-type lectin receptors in immunity and homeostasis. *Annu. Rev. Immunol.* 30:491-529.

Sasaki, Y., S. Casola, J. L. Kutok, K. Rajewsky, and M. Shmidt-Supprian. 2004. TNF family member B cell-activating factor (BAFF) receptor-dependent and -independent roles for BAFF in B cell physiology. *J. Immunol.* 173:2245-2252.

Shih, T. A., M. Roederer, and M. C. Nussenzweig. 2002. Role of antigen receptor affinity in T cell-independent antibody responses in vivo. *Nat. Immunol.* 3:399-406.

Snider, D. P. and D. M. Segal. 1989. Efficiency of antigen presentation after antigen targeting to surface IgD, IgM, MHC II, Fc gamma RII, and B220 molecules on murine splenic B cells. *J. Immunol.* 143:59-65.

Taylor, J. J., M. K. Jenkins, and KA. Pape. 2012. Heterogeneity in the differentiation and function of memory B cells. *Trends Immunol.* 33:590-7.

Ueda, Y., D. Liao, K. Yang, A. Patel, and G. Kelsoe. 2007. T-independent activation-induced cytidine deaminase expression, class-switch recombination, and antibody production by immature/transitional 1 B cells. *J. Immunol.* 178:3593-601.

Valentine, M. A., E. A. Clark, G. L. Shu, N. A. Norris, and J. A. Ledbetter. 1988. Antibody to a novel 95-kDa surface glycoprotein on human B cells induces calcium mobilization and B cell activation. *J. Immunol.* 140:4071-4078.

Weir, D. M., L. A. Herzenberg, C. Blackwell, and L. A. Herzenberg. 1986. Handbook of Experimental Immunology. 1:31.6-31.7.

Weller, S., A. Faili, C. Garcia, M. C. Braun, F. F. Le Deist, G. G. de Sainte Basile, O. Hermine, A. Fischer, C. A. Reynaud, and J. C. Weill. 2001. CD40-CD40L independent Ig gene hypermutation suggests a second B cell diversification pathway in humans. *Proc. Natl. Acad. Sci. USA.* 98:1166-70.

Yazawa, N., M. Fujimoto, S. Sato, K. Miyake, N. Asano, Y. Nagai, O. Takeuchi, K. Takeda, H. Okochi, S. Akira, T. F. Tedder, and K. Tamaki. 2003. CD19 regulates innate immunity by the Toll-like receptor RP105 signaling in B lymphocytes. *Blood* 102:1374-1380.

Zhang, J., Y. J. Liu, I. C. MacLennan, D. Gray, and P. L. Lane. 1988. *B cell memory to thymus-independent antigens type* 1 *and type* 2: the role of lipopolysaccharide in B memory induction. *Europ. J. Immunol.* 18:1417-24.

Example 2

Six to eight weeks old C57BL/6 mice were immunized with the amounts of OVA-αCD180 conjugate (i.v.), plus 20 µg of TLR7 agonist R848 (when indicated), as shown in FIG. 7, or were left untreated (naïve). At the indicated time points, serum was collected and the specific levels of IgG (FIG. 7A) and IgM (FIG. 7B) were determined by ELISA. The data show the average of 3 mice per group+SEM. These data show that as little as 17.5 µg of OVA-αCD180 can induce a strong IgG Ab response. However, when a TLR7 agonist (R848) is added, only 1.75 µg of OVA-αCD180 is needed to induce an Ag-specific response greater than that induced with 17.5 µg of OVA-αCD180 only. Thus, combinations of the conjugate and a TLR7 agonist provided synergistic induction of the IgG and IgM antibody responses.

Example 3

Six to eight weeks old C57BL/6 mice were immunized with the amounts of WNVE-αCD180 conjugate (i.v.) (using same conjugation technique as with OVA), or with live WNV-Texas strain (Tx) (f.p.), as indicated in FIG. 8. As controls, mice were immunized (i.v.) with NP/CD180 conjugates (30 µg or 15 µg+R848). At the indicated time points, serum was collected and the specific titers of IgG (FIG. 8A) and neutralizing titers (FIG. 8B) were determined by ELISA and by a plaque reduction neutralization titer (PRNT) viral neutralization assay adapted for WNV (B cells and antibody play critical roles in the immediate defense of disseminated infection by West Nile encephalitis virus. Diamond MS, Shrestha B, Marri A, Mahan D, Engle M. J Virol. 2003 February; 77(4):2578-86.), respectively. The data are an average of 2 mice per group+SEM. $PRNT_{50}$ indicates the minimal concentration of serum that reduces the number of plaques by 50% compared to controls. There was no difference between control mice immunized with 30 µg or 15 µg+R848 of NP/CD180 conjugates (not shown). These data show that mice inoculated with anti-CD180 to which purified recombinant West Nile virus (WNV) envelope (E) protein has been attached (WNVE) develop both WNVE specific IgG Abs (FIG. 8A) and neutralizing Abs to WNVE (FIG. 8B).

Example 4

Six to eight weeks old C57BL/6 mice were immunized with the amounts of WNV E protein/CD180 conjugate (E/CD180) (same as in Example 3) (i.v.), plus 20 µg R848 or 50 µg CpGB (when indicated) as shown in FIG. 9, or were infected with 1000 pfu live WNV-Tx (f.p.). As controls, mice were immunized (i.v.) with NP/CD180 conjugates (30 µg or 15 µg+R848 or CpGB). After 28 days, serum was collected and neutralizing titers were determined by PRNT assay. The data show the average of 3 mice per group+SEM. There was no difference between control mice immunized with 30 µg or 15 µg plus R848 or CpGb of NP/CD180 conjugates (not shown). These data clearly show that the WNVE-αCD180 conjugate induces a neutralizing Ab response that is enhanced by the addition of an adjuvant to TLR7 (R848) or TLR9 (CpGB). Mice infected with WNV have a higher neutralizing Ab titer, but then these mice are replicating virus and exposed to virus for a couple of weeks, not just a single injection (as with the WNVE-αCD180 conjugate injection).

Example 5

Six to eight weeks old C57BL/6 mice were immunized with 15 µg of the WNV E protein/αCD180 conjugate described above (E/CD180) plus 20 µg R848 or 50 µg CpGB (i.v.), or infected with 1000 pfu live WNV Texas (f.p.). As controls, mice were immunized (i.v.) with 15 µg NP/CD180 conjugate plus 50 µg CpGB. After 32 days (d32), mice were challenged with intracranial injection of 50 pfu of WNV Texas (i.e.). Mice were monitored for mortality for 21 days. The data show the survival/mortality of 2 mice per group. These data (see Table 1) show that B6 mice immunized with WNVE-CD180 conjugates are protected from death induced by intracranial (i.e.) injection of 50 pfu of WNV Texas strain (WNV-TX). In contrast, the mice immunized with NP/CD180+CpGB as a negative control all died by day 6.

TABLE 1

Mice immunized with WNVE-aCD180 are protected from lethal WNV challenge

| Immunization/Group | Survival after i.c. challenge with WNV-TX |
|---|---|
| 1) 1000 pfu WNV-TX (pre-exposed, pos. control) | 100% > 21 days |
| 2) NP-aCD180 + CpGB (no WNV-TX, neg. control) | 0%, all dead by day 7 p.i. |
| 3) WNVE-aCD180 + CpGB | 100% > 21 days |
| 4) WNVE-aCD180 + R848 | 50% > 21 days |

Example 6

OT-I OVA-specific CD8 T cells were transferred into C57BL/6 mice, which were then inoculated with 20 µg of αCD180/OVA conjugate (i.v.), alone or together with 50 µg of poly I:C (TLR7 agonist) or CpGB (TLR9 agonist), or with 20 µg of isotype/OVA conjugate as a negative control, or with phosphate buffered saline (PBS). On days 3, 7, and 20, OT-I T cells from peripheral blood were analyzed by gating on CD8+ cells, and Vα2 and VB5.1/5.2 The data (not shown) demonstrate that mice inoculated with Ag-specific CD8 T cells and then αCD180/OVA (without adjuvant) have an expanded frequency of Ag-specific T cells 3 days later, and then levels wane. If adjuvant is added, then more CD8 T cells expand and survive longer (See Table 2, with CpGB as the adjuvant). This demonstrates that Ag-anti-CD180 can activate and expand cytotoxic T cell responses, and combinations with adjuvant provide even better activation and expansion of the cytotoxic T cell response.

TABLE 2

Mice immunized with OVA-aCD180 with have expanded levels of Ag-specific CD8 T cells

| | % OVA Ag-specific CD8 T cells of total CD8 T on: | | |
|---|---|---|---|
| Immunization Group | Day 3 | Day 7 | Day 20 |
| 1) PBS | 1.8 | 2.1 | 2.0 |
| 2) OVA-Isotype control | 2.6 | 2.0 | 2.5 |
| 3) OVA-aCD180 | 6.0 | 2.3 | 2.5 |
| 4) OVA-aCD180 + CpGB | 9.6 | 3.0 | 3.5 |

C57BL/6 mice were inoculated day-1 with 500,000 OVA-specific CD8 T cells (OT-I Tg T cells) and on day 0 inoculated i.v. with either: 1) PBS; 2) 20 mg of OVA attached to G28-1 isotype control mAb; 3) 20 mg of OVA attached to αCD180; or 4) 20 mg of OVA attached to αCD180+50 mg CpGB adjuvant. Means are shown for 3 mice/group for each time point. Bold numbers are statistically significantly different from controls. OVA-αCD180 immunization expands CD8 T cell numbers in vivo. The expansion is not long-lasting but can be extended by the addition of adjuvant.

We claim:
1. A composition, comprising:
   (a) a CD180 targeting molecule; and
   (b) a heterologous antigen attached to the CD 180 targeting molecule.
2. The composition of claim 1, wherein the heterologous antigen is a polypeptide antigen.

3. The composition of claim 1, wherein the heterologous antigen is a polysaccharide, carbohydrate, or a glycolipid antigen.

4. The composition of claim 1, wherein the heterologous antigen is an allergen.

5. The composition of claim 1, wherein the heterologous antigen is a pathogen-specific antigen.

6. The composition of claim 5, wherein the pathogen-specific antigen comprises an antigen selected from the group consisting of a West Nile virus antigen, a hepatitis virus antigen, and a dengue virus antigen.

7. The composition of claim 1, wherein the CD180 targeting molecule is a CD180 antibody or antibody fragment.

8. The composition of claim 7, wherein the CD180 antibody or antibody fragment comprises a human or animal CD180 binding domain linked to an immunoglobulin constant region (Fc) domain that has impaired binding to human or animal Fc receptor FcγRIIb and/or to human or animal complement proteins.

9. The composition of claim 8, wherein the CD180 targeting molecule is a CD180 antibody or antibody fragment, and wherein the heterologous antigen is a polypeptide.

10. The composition of claim 1, wherein the composition further comprises an adjuvant.

11. The composition of claim 10, wherein the adjuvant is selected from the group consisting of a toll-like receptor 7 (TLR7) agonist and a toll-like receptor 9 (TLR9) agonist.

12. An isolated nucleic acid encoding the composition of claim 9.

13. A nucleic acid vector comprising the isolated nucleic acid of claim 12.

14. A recombinant host cell comprising the nucleic acid vector of claim 13.

15. A pharmaceutical composition, comprising:
   (a) the composition of claim 1; and
   (b) a pharmaceutically acceptable carrier.

16. A method for producing antibody, comprising
   (a) culturing the recombinant host cell of claim 14 under conditions suitable for expression of the nucleic-acid encoded antibody composition; and
   (b) isolating the antibody composition from the cultured cells.

17. A method for treating or limiting development of a disorder, comprising administering to an individual at risk of a disorder or having a disorder, an amount effective to treat or limit development of the disorder of the composition of claim 1.

18. The method of claim 17, where the individual has a T-cell deficiency and/or a defect in co-stimulation between B cells and T cells.

19. The method of claim 17, wherein the individual is a neonate or is elderly.

20. The method of claim 17, wherein the individual has an allergy.

* * * * *